US011174466B2

(12) United States Patent
Bean et al.

(10) Patent No.: US 11,174,466 B2
(45) Date of Patent: Nov. 16, 2021

(54) PRODUCTION OF VIRUSES IN CELL CULTURE

(71) Applicants: Commonwealth Scientific and Industrial Research Organisation, Acton (AU); University of Georgia Research Foundation, Inc., Athens, GA (US)

(72) Inventors: Andrew Bean, Ocean Grove (AU); John William Lowenthal, Belmont (AU); Luis Fernando Malaver-Ortega, Glen Waverly (AU); Ralph A. Tripp, Watkinsville, GA (US)

(73) Assignees: Commonwealth Scientific and Industrial Research Organisation, Acton (AU); University of Georgia Research Foundation, Inc., Athens, GA (US)

( * ) Notice: Subject to any disclaimer, the term of this patent is extended or adjusted under 35 U.S.C. 154(b) by 394 days.

(21) Appl. No.: 15/777,890

(22) PCT Filed: Nov. 23, 2016

(86) PCT No.: PCT/AU2016/051147
§ 371 (c)(1),
(2) Date: May 21, 2018

(87) PCT Pub. No.: WO2017/088018
PCT Pub. Date: Jun. 1, 2017

(65) Prior Publication Data
US 2018/0340153 A1    Nov. 29, 2018

(30) Foreign Application Priority Data
Nov. 24, 2015 (AU) ................................ 2015904851

(51) Int. Cl.
| C12N 7/02 | (2006.01) |
| A61K 39/12 | (2006.01) |
| C12N 7/00 | (2006.01) |
| A61K 39/145 | (2006.01) |
| A61K 39/17 | (2006.01) |

(52) U.S. Cl.
CPC ............... *C12N 7/02* (2013.01); *A61K 39/12* (2013.01); *A61K 39/145* (2013.01); *A61K 39/17* (2013.01); *C12N 7/00* (2013.01); *C12N 2760/16051* (2013.01); *C12N 2760/16052* (2013.01); *C12N 2760/16134* (2013.01); *C12N 2760/16151* (2013.01); *C12N 2760/16152* (2013.01); *C12N 2760/16234* (2013.01); *C12N 2760/16334* (2013.01); *C12N 2760/18251* (2013.01)

(58) Field of Classification Search
None
See application file for complete search history.

(56) References Cited

U.S. PATENT DOCUMENTS

| 5,162,215 A | 11/1992 | Bosselman et al. |
| 7,145,057 B2 | 12/2006 | Van de Lavoir et al. |
| 2002/0081614 A1 | 6/2002 | Case et al. |
| 2003/0021776 A1 | 1/2003 | Rebar et al. |
| 2006/0206952 A1 | 9/2006 | Van de Lavoir et al. |
| 2006/0246567 A1 | 11/2006 | Rebar et al. |
| 2007/0004667 A1 | 1/2007 | McSwiggen et al. |
| 2008/0182332 A1 | 7/2008 | Cai et al. |
| 2010/0291048 A1 | 11/2010 | Holmes et al. |
| 2012/0282674 A1 | 11/2012 | Machuy et al. |
| 2013/0123484 A1 | 5/2013 | Liu et al. |
| 2018/0340154 A1 | 11/2018 | Bean et al. |

FOREIGN PATENT DOCUMENTS

| CN | 104560864 | 4/2015 |
| CN | 104694576 | 6/2015 |
| EP | 2975119 | 1/2016 |
| IN | 3763/CHE/2012 | 3/2014 |
| WO | WO 1999064068 | 12/1999 |
| WO | WO 2002057308 | 7/2002 |
| WO | WO 2005113756 | 12/2005 |
| WO | WO 2007064802 | 6/2007 |
| WO | WO 2009036510 | 3/2009 |
| WO | WO 2011072247 | 1/2011 |
| WO | WO 2011017293 | 2/2011 |
| WO | 2011029914 | 3/2011 |
| WO | WO 2011005765 | 6/2011 |
| WO | 2012164130 | 6/2012 |

(Continued)

OTHER PUBLICATIONS

Carvajal-Yepes et al., Human Vaccines & Immunotherapeutics, Sep. 2015, 11(9):2296-2304. (Year: 2015).*
Ge et al., J. Virology, 2007, 81 (1):150-158. (Year: 2007).*
Takaoka et al., Science, Jun. 2000, 288(5475):2357-2360. (Year: 2000).*
Horai, et al. (1998) "Production of Mice Deficient in Genes for Interleukin (IL)-1α, IL-1β, IL-1α/β, and IL-1 Receptor Antagonist Shows that IL-1β Is Crucial in Turpentine-induced Fever Development and Glucocorticoid Secretion"; J Exp Med. May 4, 1998;187(9); pp. 1463-1475.
Park TS, et al. (2014) "Targeted gene knockout in chickens mediated by TALENs"; Proc Natl Acad Sci U S A. 111 (35); p. 12716-12721.

(Continued)

*Primary Examiner* — Stacy B Chen
(74) *Attorney, Agent, or Firm* — Carol L. Francis; Bozicevic, Field & Francis LLP

(57) ABSTRACT

The present invention relates to methods of replicating viruses in vitro. In particular, the invention relates to a genetically modified population of cells, and/or a population of cells treated with an exogenous compound, wherein the cells are capable of producing more virus than cells lacking the genetic modification and/or lacking treatment with the exogenous compound. The invention also relates to methods of producing populations of such cells, as well as the use of the viruses obtained to prepare vaccine compositions.

11 Claims, 15 Drawing Sheets

(56) References Cited

FOREIGN PATENT DOCUMENTS

Figure 1:
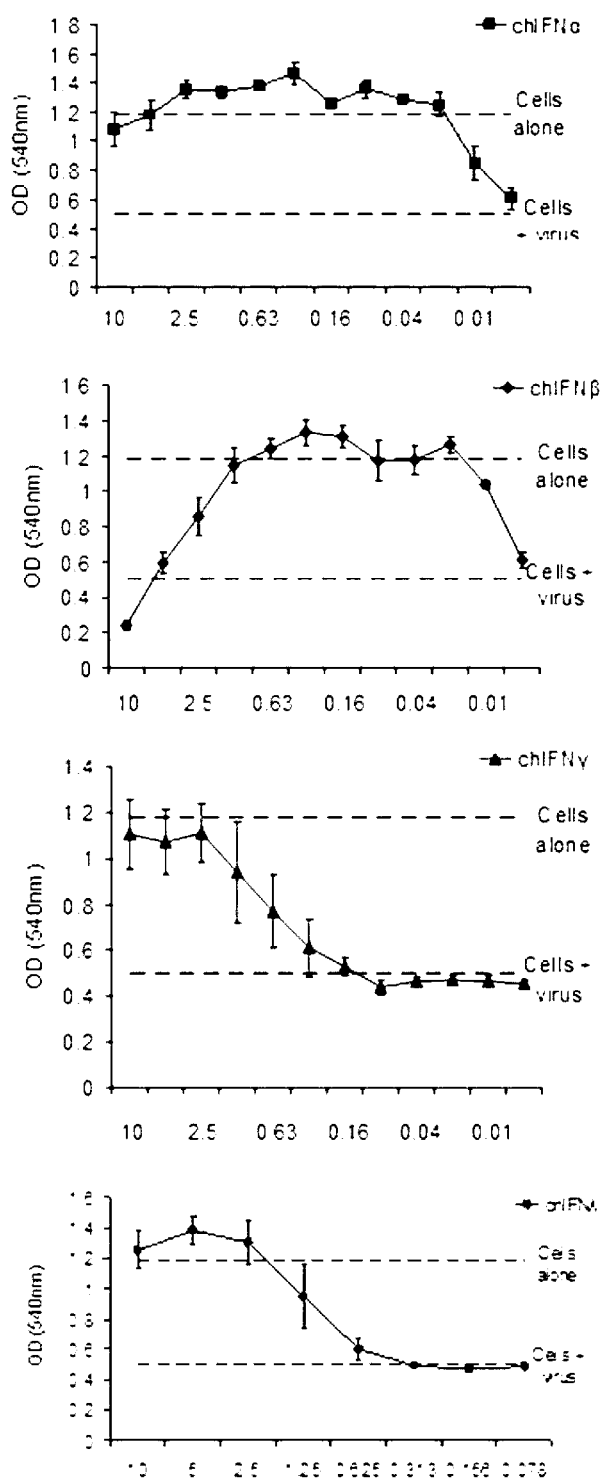

| WO | WO 2013155572 | 10/2013 |
| --- | --- | --- |
| WO | WO 2013166264 | 11/2013 |
| WO | WO 2014123 967 | 8/2014 |
| WO | WO 2014142433 | 9/2014 |
| WO | WO 2014189628 | 11/2014 |
| WO | WO 2014195692 | 12/2014 |
| WO | WO 2014199166 | 12/2014 |

OTHER PUBLICATIONS

Partial European Search Report dated Apr. 4, 2019 for EP 16867451.3.
Partial European Search Report dated May 27, 2019 for EP 16867450.5.
Véron N, et al. (2015) "CRISPR mediated somatic cell genome engineering in the chicken"; Dev Biol. 407(1); pp. 68-74.
Dominguez et al., (2005), "Phenotypic and Biochemical Analyses of BACE1- and BACE2-deficient Mice", The Journal of Biological Chemistry, 280(35):30797-30806.
Gao et al., (2013), "Cytokine and Chemokine Profiles in Lung Tissues fromFatal Cases of 2009 Pandemic Influenza A (H1N1)", The American Journal of Pathology, 183(4): 1258-1268.
Hill-Batorski et al., (2015), "Loss of Interleukin 1 Receptor Antagonist Enhances Susceptibility to Ebola Virus Infection", The Journal of Infectious Diseases, 212:S329-S335.
Karpala et al., (2011), "Characterization of Chicken Mda5 Activity: Regulation of IFN-B in the Absence of RIG-I Functionality", J Immunol, 186:5397-5405.
Lu et al., (2013), "Melanoma Differentiation-Associated Gene 5 Senses Hepatitis B Virus and Activates Innate Immune Signaling To Suppress Virus Replication", J Immunol, 191:3264-3276.
Extended European Search Report for European application No. 16867450.5, dated Oct. 3, 2018, pp. 1-19.
U.S. Appl. No. 15/777,897, filed May 21, 2018, Bean, et al.
Balciunas et al. (2006) "Harnessing a high cargo-capacity transposon for genetic applications in vertebrates"; PLoS Genet. 2(11); e169.
Bannister et al. (2007) "Comparison of chicken 7SK and U6 RNA polymerase III promoters for short hairpin RNA expression"; BMC Biotechnology. pp. 7 :79.
Bird et al. (1988) "Single-chain antigen-binding proteins" Science 242; pp. 423-426.
Bosselman et al. (1989) "Germline transmission of exogenous genes in the chicken"; Science, 243; pp. 533-534.
Carvajal-Yepes, M. et al. (2015) "Enhanced production of human influenza virus in PBS-12SF cells with a reduced interferon response"; Human Vaccines and Immunotherapeutics, 11(19); pp. 2296-2304.
Cong et al. (2013) "Multiplex genome engineering using CRISPR/Cas systems"; Science 339; pp. 819-823.
De Coupade et al. (2005) "Novel human-derived cell-penetrating peptides for specific subcellular delivery of therapeutic bio molecules"; Biochem J. 390; pp. 407-418.
Hamamoto, I et al. (2013) "High yield production of influenza virus in Madin Darby canine kidney (MDCK) cells with stable knockdown of IRF7"; PloS One, 8(3); e59892; pp. 1-12.
Harmsen and De Haard (2007) "Properties, production, and applications of camelid single-domain antibody fragments"; Appl Microbiol Biotechnol. 77; pp. 13-22.
Himly et al. (1998) "The DF-1 chicken fibroblast cell line: transformation induced by diverse oncogenes and cell death resulting from infection by avian leukosis viruses"; Virology. 248(2); pp. 295-304.
Hoffmann et al. (2002) "Eight-plasmid system for rapid generation of influenza virus vaccines"; Vaccine 20; pp. 3165-3170.
Huston et al. (1988) "Protein engineering of antibody binding sites: recovery of specific activity in an anti-digoxin single-chain Fv analogue produced in Escherichia coli"; Proc Natl Acad Sci. USA. 85; pp. 5879-5883.

International Search Report and Written Opinion for PCT/AU2016/051147 dated Jan. 24, 2017, 15 pages.
International Search Report and Written Opinion for PCT/AU2016/051146 dated Jan. 24, 2017, 18 pages.
Jones et al. (1986) "Replacing the complementarity-determining regions in a human antibody with those from a mouse"; Nature 321:522-525.
Jones (2008) "Biomaterials as vaccine adjuvants"; Biotechnolo Prog. 24; pp. 807-814.
Josefsberg et al. (2012) "Vaccine process technology"; Biotech and Bioengineering. 109(9); pp. 1443-1460.
Kawakami et al. (2000) "Identification of a functional transposase of the Tol2 element, an Ac-like element from the Japanese medaka fish, and its transposition in the zebrafish germ lineage"; Proc Natl Acad Sci USA, 97; 11403-11408.
Koga, et al. (1996) "Transposable element in fish"; Nature 383:30.
Koppelhus et al. (2008) "Improved cellular activity of antisense peptide nucleic acids by conjugation to a cationic peptide-lipid (CatLip) domain"; Bioconj Chem. 19; pp. 1526-1534.
Lavitrano et al. (1989) "Sperm cells as vectors for introducing foreign DNA into eggs: genetic transformation of mice"; Cell 57; pp. 717-723.
Makarova et al. (2015) "An updated evolutionary classification of CRISPR-Cas systems"; Nature Reviews Microbiology 13(11); pp. 1-15.
Massin et al. (2005) "Cloning of the chicken RNA polymerase I promoter and use for reverse genetics of influenza A viruses in avian cells"; J Virol. 79(21); p. 13811-13816.
Milián et al. (2015) "Current and emerging cell culture manufacturing technologies for influenza vaccines"; BioMed Research International 2015; pp. 1-11.
Morrison et al. (1984) "Chimeric human antibody molecules: mouse antigen-binding domains with human constant region domains"; Proc Natl Acad Sci USA 81; pp. 6851-6855.
Muyldermans (2001) "Single domain camel antibodies: current status"; J Biotechnol. 74; pp. 277-302.
Ran et al. (2013) "Genome engineering using the CRISPR-Cas9 system"; Nature Protocols. 8(11); pp. 2281-2308.
Schusser et al. (2013) "Immunoglobulin knockout chickens via efficient homologous recombination in primordial germ cells"; Proc Natl Acad Sci USA 110(50); p. 20170-20175.
Smith et al. (2008) Vaccine. 26(29-30); pp. 3778-3782.
Thoraval et al. (1995) "Germline transmission of exogenous genes in chickens using helper-free ecotropic avian leukosis virus-based vectors"; Transgenic Research 4; pp. 369-377.
Zetsche et al. (2015) "Cpf1 is a single RNA-guided endonuclease of a class 2 CRISPR-Cas system"; Cell 163; pp. 1-3.
Zhang et al. (2011) "Efficient construction of sequence-specific TAL effectors for modulating mammalian transcription"; Nature Biotechnology 29; pp. 149-153.
Takeuchi, Osamu and AKIRA, Shizuo, (2008) "MDA5/RIG-I and virus recognition", Current Opinion in Immunology, 20:17-22.
Zhou, et al., (2013) Interferon Induced IFIT Family Genes in Host Antiviral Defense, Int. J. Biol. Sci., 9(2):200-208.
Apperley., (2012), "The Importance of Innate Resistance Genes in Respiratory Syncytial Virus Replication in Airway Epithelial Cells", 1-188.
Benitez et al., (2015), "In Vivo RNAi Screening Identifies MDA5 as a Significant Contributor to the Cellular Defense against Influenza A Virus", Cell Reports, 1714-1726.
Broquet et al., (2010), "RIG-1/MDAS/MAVS Are Required To Signal a Protective IFN Response in Rota virus-Infected Intestinal Epithelium", The Journal of Immunology, 186:1618-1626.
Cao et al., (2014), "MDAS plays a critical role in interferon response during hepatitis C virus infection", Journal of Hepatology, 62:771-778.
Coyne et al., (2011), "Comparative RNAi Screening Reveals Host Factors Involved in Enterovirus Infection of Polarized Endothelial Monolayers", Cell Host & Microbe, 9:70-82.
Datta et al., (2011), "Mechanism of HCV's resistance to IFN-a in cell culture involves expression of functional IFN-a receptor 1", Virology Journal, (8)351:1-18.

(56) References Cited

OTHER PUBLICATIONS

Dear et al., (2001), "Identification and characterization of two novel calpain large subunit genes", Gene 274, 245-252.
Hassan et al., (2014), "Inositol-requiring Enzyme 1 Inhibits Respiratory Syncytial Virus Replication*", Journal of Biological Chemistry, 289(11):7537-7547.
Lin et al., (2017), "CNOT4-Mediated Ubiquitination of Influenza A Virus Nucleoprotein Promotes Viral RNA Replication", American Society for Microbiology, 8(3):1-16.
Nasirudeen et al., (2011), "RIG-I, MDAS and TLR3 Synergistically Play an Important Role in Restriction of Dengue Virus Infection", PLoS, 5(1):1-11.
Van Der Sanden et al., (2005), "Engineering Enhanced Vaccine Cell Lines To Eradicate VaccinePreventable Diseases: the Polio End Game", Journal of Virology, 90(4): 1694-1704.
Xiang et al., (2015), "Identification of Cholesterol 25-Hydroxylase as a Novel Host Restriction Factor and a Part of the Pritnary Innate Immune Responses against Hepatitis C Virus Infection", Journal of Virology, 89(13):6805-6816.
Zhao et al., (2011), "A functional genomic screen reveals novel host genes that mediate interferon-alpha's effects against hepatitis C virus", Journal of Hepatology, 56:326-333.
Extended European Search Report for European Application No. 16867451.3, dated Jan. 14, 2020 39 pages.
U.S. Appl. No. 16/258,099, filed Jan. 25, 2019, Bean, et al.
U.S. Appl. No. 16/258,229, filed Jan. 25, 2019, Bean, et al.
Chung et al. (1993) "A 5' element of the chicken beta-globin domain serves as an insulator in human erythroid cells and protects against position effect in *Drosophila*"; *Cell*. 74(3)', pp. 505-514.
Costantini et al. (2008) "Peptide motifs for insertion of radiolabeled biomolecules into cells and routing to the nucleus for cancer imaging or radiotherapeutic applications"; *Cancer Biotherm Radiopharm* 23(1); pp. 3-24.
Deshayes et al. (2008) "Delivery of proteins and nucleic acids using a non-covalent peptide-based strategy"; *Adv Drug Deliv Rev*. 60; pp. 537-547.
Genzel et al. (2009) "Continuous cell lines as a production system for influenza vaccines"; Expert Rev Vaccines. 8(12); pp. 1681-1692.
Genzel (2015) "Designing cell lines for viral vaccine production: Where do we stand?"; Biotechnol J. 10(5); pp. 728-740.
Grein et al. (2013) "Membrane Supported Virus Separation from Biological Solutions"; Chemie Ingenieur Technik 85(8); pp. 1183-1192.
Horimoto et al. (2006) "Strategies for developing vaccines against H5N1 influenza A viruses.Trends"; *Mol Med* 12(11); pp. 506-514.
Horimoto et al. (2007) "Enhanced growth of seed viruses for H5N1 influenza vaccines"; *Virology* 266(1); pp. 23-27.
Howl et al. (2007) "The many futures for cell-penetrating peptides: how soon is now?"; *Biochem Soc Trans*. 35:767-769.
IPRP dated May 29, 2018 for PCT/AU2016/051146.
IPRP dated May 29, 2018 for PCT/AU2016/051147.
Kalbfuss et al. (2006) "Purification of cell culture-derived human influenza A virus by size exclusion and anion-exchange chromatography"; *Biotechnol Bioeng*. 96(5); pp. 932-944.
Lodish et al. (2000) "Recombination between Homologous DNA Sites"; *Molecular Cell Biology 4th Edition. New York, Section 12.5*.
Lowenthal et al. (1995) "Production of interferon-gamma by chicken T cells"; *J Interferon Cytokine Res*. 15(11); pp. 933-938.
Meyer-Losic et al. (2006) "Improved therapeutic efficacy of doxorubicin through conjugation with a novel peptide drag delivery technology (Vectocell)"; J Med Chem. 49; pp. 6908-6916.
Montomoli et al. (2012) "Cell culture-derived influenza vaccines from Vero cells: a new horizon for vaccine production"; *Expert Rev Vaccines*. 11(5); pp. 587-594.
Reed and Muench (1938) "A Simple Method Of Estimating Fifty Per Cent Endpoints"; *The American Journal of Hygiene* 27; pp. 493-497.
Rodrigues et al. (2015) "Viral vaccines and their manufacturing cell substrates: New trends and designs in modern vaccinology"; *Biotechnol J*. 10(9); pp. 1329-1344.

Sander and Joung (2014) "CRISPR-Cas systems for editing, regulating and targeting genomes"; Nat Biotechnol.32(4); pp. 347-355.
Stewart et al. (2014) "Inhibitors of the interferon response enhance virus replication in vitro"; PLoS One.9(11): e112014; pp. 1-8.
Tibary et al. (2007) "Current knowledge and future challenges in camelid reproduction"; Soc Reprod Fertil Suppl. 64; pp. 297-313.
Tripp et al. (2015) "Engineering enhanced vaccine cell lines to eradicate vaccine preventable diseases: the polio endgame (VAC9P. 1107)"; J Immunol. 194 (1 Supplement) 145.15; 1 page.
Visintin et al. (2008) "In vivo selection of intrabodies specifically targeting protein-protein interactions: a general platform for an "undruggable" class of disease targets"; *J Biotechnol*. 135; pp. 1-15.
Weaver (2002) "The RecBCD Pathway for Homologous Recombination"; *Molecular Biology 2nd Edition, New York, Section 22.1*; pp. 710-712.
Wolf et al. (2008) "Downstream Processing: From Egg to Cell Culture-Derived Influenza Virus Particles"; *Chem Eng Technol*. 31(6); pp. 846-867.
Wolf et al. (2011) "Downstream processing of cell culture-derived virus particles"; Expert Rev Vaccine. 10 (10); pp. 1451-1475.
Tizard et al. (2014) "Precision genome engineering in the chicken: the gap between science and market place", presented at the Proceeding of the 2nd International Workshop on the Regulation of Animal Biology, IWRAB-II, Brasilia, Aug. 18-21, 2014, published online Sep. 1, 2014, 21 pages.
Urwin (Jan. 16, 2014) "Would you prefer to eat genetically modified eggs, or see day-old chicks destroyed?" The Guardian, published online at https://www.theguardian.com/commentisfree/2014/jan/17/would-you-prefer-to-eat-genetically-modified-eggs-or-see-day-old-chicks-destroyed, 3 pages.
Woelders (Sep. 8, 2014) "Alternatives for killing day-old male chicks", Symposium Presentation published online via the Wageningen University & Research Website at http://edepot.wur.nl/313906, 31 pages.
Genbank Accession NM_000577 IL 1RN, (2019) "*Homo sapiens* interleukin 1 receptor antagonist (IL1RN), transcript variant 3, mRNA", NCBI Reference Sequence: NM_000577.5, 3 pages.
Genbank Accession NM_205485 IL-1RA, (2018) "Gallus gallus interleukin 1 receptor type 1 (IL1R1), mRNA", NCBI Reference Sequence: NM_205485.1, 3 pages.
Ge et al., (2007) "Newcastle Disease Virus-Based Live Attenuated Vaccine Completely Protects Chickens and Mice from Lethal Challenge of Homologous and Heterologous H5N1 Avian Influenza Viruses", Journal of Virology, 81(1):150-158.
Sid, Hicham and Schusser, Benjamin, (2018) "Applications of Gene Editing in Chickens: A New Era Is on the Horizon", Front Genet, 9(456):1-12.
Ceasar, S. Antony, et al., (2016) "Insert, remove or replace: A highly advanced genome editing system using CRISPR/Cas9", Biochimica et Biophysica Acta 1863, 2333-2344.
Mucha, Olga, et al., (2018) "Pharmacological versus genetic inhibition of heme oxygenase-1—the comparison of metalloporphyrins, shRNA and CRISPR/Cas9 system", Acta Biochimica Polonica, 65(2):277-286.
Podolska, Katerina and Svoboda, Petr, (2011) "Targeting genes in living mammals by RNA interference", Briefings in Functional Genomics, 10(4):238-247.
Strecket, Jonathan, et al., (2019) "RNA-guided DNA insertion with CRISPR-associated transposases". Science, 365:45-53.
Tanaka, Masato, et al., (1999) "Embryonic Lethality, Liver Degeneration, and Impaired NF-kB Activation in IKK-b-Deficient Mice", Immunity, 10:421-429.
Yamaoka, Kunihiro, et al., (2004) "The Janus kinases (Jaks)", Genome Biology, 5(12):253.
Hwang et al., (1995) "A null mutation in the gene encoding a type I interferon receptor component eliminates anti proliferative and antiviral responses to interferons alpha and beta and alters macrophage responses.", PNAS, 92(24):11284-11288.

* cited by examiner

A

B

PRODUCTION OF VIRUSES IN CELL CULTURE

FIELD OF THE INVENTION

The present invention relates to methods of replicating viruses in vitro. In particular, the invention relates to a genetically modified population of cells, and/or a population of cells treated with an exogenous compound, wherein the cells are capable of producing more virus than cells lacking the genetic modification and/or lacking treatment with the exogenous compound. The invention also relates to methods of producing populations of such cells, as well as the use of the viruses obtained to prepare vaccine compositions.

BACKGROUND OF THE INVENTION

Viral infection remains an important health problem in both humans and in economically important livestock with adverse economic and social consequences.

One of the main approaches to protecting animals from viral disease is vaccination. Availability of sufficient quantities of virus, and the cost associated with virus production are limiting factors for the production of vaccines. There are current limitations with the production of influenza vaccine, and other vaccines, due to the reliance on an abundant supply of eggs. This is a particular issue when faced with producing enough vaccine to combat an emerging pandemic or to stockpile vaccine for pandemic preparedness. In addition, some virus are produced in cell culture systems which provide greater scalability options for pandemic preparedness. However, not all viruses replicate well in existing cell lines and thus are often not replicated at sufficient titres for cost effective vaccine production. Further, different strains of the same virus have different replication efficiencies in the same cell line which can limit the amount of vaccine produced and increase the cost of vaccine production in instance where viral replication is low.

Thus, there is a need to develop improved methods and cell populations for producing virus for vaccine production. In particular, there is a need to increase virus production in existing cell lines and to develop new cell lines for producing high virus yield and suitable for rapid scaling of size to meet the requirements for vaccine production for emerging pandemics and pandemic preparedness. It is against this background that the present inventors have developed a method and population of cells for replicating a virus in vitro.

SUMMARY OF THE INVENTION

The present inventors have demonstrated that reducing the expression of an antiviral gene, and/or the level of antiviral protein activity in a cell in vitro, can increase viral production in a cell.

Thus, in one aspect, the present invention provides a method of replicating a virus, the method comprising;

1) obtaining a population of cells having a genetic modification which reduces the expression of an antiviral gene in the cells when compared to isogenic cells lacking the genetic modification, 2) inoculating the cells in vitro with the virus, and 3) culturing the cells for a predetermined period of time to replicate the virus, wherein the cells are capable of producing more virus than a population of the isogenic cells.

In embodiment, the genetic modification is in the genome of the cell. In an embodiment, the genome is homozygous for the genetic modification. In an embodiment, the genetic modification is in the mitochondrial DNA (mtDNA) or nuclear DNA. In an embodiment, the genetic modification is introduced into 100% the population of cells.

The genetic modification can be any change to a naturally occurring cell that achieves the desired effect of reducing the expression of an antiviral gene, and/or the level of antiviral protein activity in the population of cells.

In an embodiment, the genetic modification is a deletion, substitution or an insertion into the antiviral gene or a regulatory region thereof. For example, the genetic modification can have been introduced by a programmable nuclease. In another example, the genetic modification can have been introduced by homologous recombination so that it no longer encodes a protein with antiviral activity such as by deleting part or all of the antiviral gene, inserting an exogenous polynucleotide into the antiviral gene, or rearranging the orientation of some of the antiviral gene (such as an exon). In another embodiment, the genetic modification was introduced by non-homologous end joining. In yet a further embodiment, the genetic modification was introduced by a chemical mutagen.

In an embodiment, the genetic modification is a point mutation.

In an embodiment, the genetic modification was introduced by a transgene which encodes a polynucleotide which reduces the expression of an antiviral gene, and/or the level of antiviral protein activity in the population of cells. Examples of polynucleotides includes, but is not limited to, an antisense polynucleotide, a sense polynucleotide, a microRNA, a polynucleotide which encodes a polypeptide which binds a protein encoded by the antiviral gene, a transposon, an aptamer, a double stranded RNA molecule or a processed RNA molecule derived therefrom.

In an embodiment, the transgene comprises an open reading frame encoding the polynucleotide operably linked to a promoter which directs expression of the polynucleotide in the population of cells.

In an aspect, the present invention also provides a method of replicating a virus, the method comprising 1) obtaining a population of cells, 2) administering the cells with a exogenous compound which reduces the expression of an antiviral gene and/or reduces the level of antiviral protein activity in the cells when compared to an isogenic cells lacking the compound, 3) inoculating the cells in vitro with the virus, and 4) incubating the cells for a predetermined period of time to replicate the virus, wherein the cells are capable of producing more virus than a population of the isogenic cells.

In an embodiment, the compound is a small carbon based molecule, a protein binding agent, a programmable nuclease, a polynucleotide or a combination of two or more thereof.

In an embodiment, the protein binding agent or the polynucleotide is expressed from a transgene administered to the cell.

In an embodiment, the transgene is present in a virus to be cultured in the cell.

In an embodiment, the antiviral gene and/or protein is selected from one, two, three, four or more of: DDI2, HSBP1, GNAZ, NPR2, CNOT4, MDA5, IFNα, IL-6, IFNAR1, IFNβ, IFNγ, IFNλ, UBE1DC1, CDX2, LOC100859339, IL28RA, ZFPM2, TRIM50, DNASEIL2, PHF21A, GAPDH, BACE2, PCGF5, IL-1RA, CAPN13, UBA5, IFIH1, LAMP1, EFR3A, ARRDC3, ABI1, SCAF4, GADL1, ZKSCAN7, PLVAP, RPUSD1, CYYR1, UPF3A, ASAP1, NXF1, TOP1MT, RALGAPB, SUCLA2, GORASP2, NSUN6, CELF1, ANGPTL7, SLC26A6, WBSCR27, SIL1, HTT, MYOC, TM9SF2, CEP250, FAM188A, BCAR3, GOLPH3L, HN1, ADCY7, AKAP10, ALX1, CBLN4, CRK, CXORF56, DDX10, EIF2S3, ESF1, GBF1, GCOM1, GTPBP4, HOXB9, IFT43, IMP4, ISY1, KIAA0586, KPNA3, LRRIQ1, LUC7L, MECR, MRPL12, POLR3E, PWP2, RPL7A, SERPINH1, SLC47A2, SMYD2, STAB1, TTK, WNT3, XPO1, AHHR, ZNF334, SSR4, KLRC1, SIX5, TCL1B, ZNF211, MAGEL2, SBN01, OR1D5, SLC17A9, ZNF607, GCET2, TMEM223, ZNF146, NLRP13, RLN2, NCR2, OR4B1, GLUD2, IFNAR2, IFNGR1, INFGR2, IL-10R2, IFNκ, IFNΩ, IL-1RB and HTRA4.

In an embodiment, the antiviral gene and/or protein is selected from one, two, three, four or all of: DDI2, HSBP1, GNAZ, NPR2, CNOT4, MDA5, IFNα, IL-6, IFNAR1, IFNβ, IFNγ, IFNλ.

In an embodiment, the antiviral gene and/or protein is selected from one, two, three, or all of: DDI2, HSBP1, GNAZ, NPR2.

In an embodiment, the antiviral gene and/or protein is IL-6. In an embodiment, the antiviral gene and/or protein is MDA5. In an embodiment, the antiviral gene and/or protein is CNOT4. In another embodiment, the antiviral gene and/or protein is IFNα. In an embodiment, the antiviral gene and/or protein is DDI2. In an embodiment, the antiviral gene and/or protein is HSBP1. In an embodiment, the antiviral gene and/or protein is GNAZ. In an embodiment, the antiviral gene and/or protein is NPR2.

In an embodiment, the antiviral gene and/or protein is in the Type I, Type II or Type III interferon pathway. In an embodiment, the antiviral gene and/or protein is in the Type I interferon pathway.

In an embodiment, the cells are from a continuous cell line. In an embodiment, the cells are adherent cells. In an embodiment, the cells are non-adherent cells (suspension cells).

In an embodiment, the cells are:
1) from a primary cell line derived from chicken embryonic fibroblast (CEF);
2) from a primary cell line derived from a chicken tissue,
3) from an immortalized cell line from a chicken;
4) from embryonic-derived stem cell line EB14;
5) from embryonic-derived stem cell line EB66;
6) from the immortalized chick embryo cell line PBS-1;
7) from the chicken fibroblast cell line DF-1;
8) Madin-Darby canine kidney (MDCK) cells;
9) African green monkey kidney-derived Vero cells;
10) human retina derived PER.C6 cells; or
11) from the MRC-5 diploid cell line.

In an embodiment, the cells are cultured in the absence of serum.

In an embodiment, the virus is an animal virus. In an embodiment, the animal is a human, chicken, pig, fish, sheep or cow. In an embodiment, the animal is a human. In an embodiment, the virus is in a family selected from: Orthomyxoviridae, Herpesviridae, Paramyxoviridae, Flaviviridae and Coronaviridae.

In an embodiment, the virus in selected from: Influenza virus, Canine distemper virus, Measles virus, Reovirus, Eastern equine encephalitis virus, Canine parainfluenza virus, Rabies virus, Fowlpox virus, Western equine encephalitis virus, Mumps virus, Equine encephalomyelitis, Rubella virus, Egg drop syndrome virus, Avian oncolytic viruses, Avian infectious laryngotracheitis Herpesvirus, Newcastle disease virus, Bovine parainfluenza virus, Smallpox virus, Infectious bursal disease, Bovine Ibaraki virus, Recombinant poxvirus, Avian adenovirus type I, II or III, Swine Japanese encephalitis virus, Yellow fever virus, Herpes virus, Sindbis virus, Infections bronchitis virus, Semliki forest virus, Encephalomyelitis virus, Venezuelan EEV virus, Chicken anaemia virus, Marek's disease virus, Parvovirus, Foot and mouth disease virus, Porcine reproductive and respiratory syndrome virus, Classical swine fever virus, Bluetongue virus, Kabane virus, Infectious salmon anaemia virus, Infectious hematopoietic necrosis virus, Viral haemorrhagic septicemia virus and Infectious pancreatic necrosis virus.

In a preferred embodiment, the virus is in the Orthomyxoviridae family Thus, in an embodiment, the present invention provides a method of replicating a virus, the method comprising
1) obtaining a population of cells having a genetic modification which reduces the expression of an antiviral gene in the cells when compared to isogenic cells lacking the genetic modification,
2) inoculating the cells in vitro with the virus, and
3) culturing the cells for a predetermined period of time to replicate the virus, wherein the cells are capable of producing more virus than a population of the isogenic cells, and wherein the virus is in the Orthomyxoviridae family.

In an embodiment, the Orthomyxoviridae virus is selected from an Influenza A virus, Influenza B virus, and Influenza C virus.

In an embodiment, the Influenza A virus is selected from: H1N1, H1N2, H1N3, H1N4, H1N5, H1N6, H1N7, H1N9, H2N1, H2N2, H2N3, H2N4, H2N5, H2N7, H2N8, H2N9, H3N1, H3N2, H3N3, H3N4, H3N5, H3N6, H3N8, H4N1, H4N2, H4N3, H4N4, H4N5, H4N6, H4N8, H4N9, H5N1, H5N2, H5N3, H5N6, H5N7, H5N8, H5N9, H6N1, H6N2, H6N3, H6N4, H6N5, H6N6, H6N7, H6N8, H6N9, H7N1, H7N2, H7N3, H7N4, H7N5, H7N7, H7N8, H7N9, H9N1, H9N2, H9N3, H9N5, H9N6, H9N7, H9N8, H10N1, H10N3, H10N4, H10N6, H10N7, H10N8, H10N9, H11N2, H11N3, H11N6, H11N9, H12N1, H12N4, H12N5, H12N9, H13N2, H13N6, H13N8, H13N9, H14N5, H15N2, H15N8, H15N9 and H16N3

In an alternate preferred embodiment, the virus is in the Paramyxoviridae family. Thus, in an embodiment the present invention provides a method of replicating a virus, the method comprising
1) obtaining a population of cells having a genetic modification which reduces the expression of an antiviral gene in the cells when compared to isogenic cells lacking the genetic modification,
2) inoculating the cells in vitro with the virus, and
3) culturing the cells for a predetermined period of time to replicate the virus, wherein the cells are capable of producing more virus than a population of the isogenic cells and wherein the virus is in the Paramyxoviridae family In an embodiment, the Paramyxoviridae virus is Newcastle disease virus.

In an embodiment, the virus is the Influenza A virus.

In an embodiment, the method further comprises harvesting the replicated virus or virus particles thereof. In an embodiment, the method further comprises harvesting the replicated virus or particles thereof from secretions of the cells. In an embodiment, particles includes split virus particles and subunit virus particles.

In an aspect, the present invention provides a virus produced using the method as described herein. In an embodiment, the virus is the Influenza virus.

In an aspect, the present invention provides a method of producing a vaccine composition, the method comprising 1) replicating a virus using a method as herein described,
2) harvesting the replicated virus or particles thereof from the cells, and
3) preparing a vaccine composition from the harvested virus.

In an embodiment, step 2) or step 3) comprises inactivating the virus. In an embodiment, inactivating the virus comprises UV, heat or chemical inactivation.

In an embodiment, step 2) or step 3) comprises disruption of the virus to produce split virus particles or subunit virus particles.

As the skilled person will appreciate, methods of producing a vaccine composition of the invention can be performed using standard techniques in the art.

In an embodiment, harvesting the replicated virus or particles thereof comprises one or more of the following steps:
1) clarification, 2) concentration, 3) inactivation, 4) nuclease treatment, 5) separation/purification, 6) polishing; and/or 7) sterile filtration.

Also provided is a vaccine composition produced using the methods as described herein.

In yet another aspect, the present invention provides a population of cells in vitro comprising a genetic modification which reduces the expression of an antiviral gene in the cells when compared to isogenic cells lacking the genetic modification, wherein the cells are capable of producing more virus than a population of the isogenic cells.

In still a further aspect, the present invention provides a method of producing a population of cells as described herein, the method comprising
1) introducing the genetic modification into one or more cells,
2) screening the cells produced from step 1) for the ability to produce more virus than an isogenic cell lacking the lacking the genetic modification,
3) selecting one or more cells with a genetic modification which produce more virus than an isogenic cell lacking the lacking the genetic modification, and
4) optionally clonally expanding the selected cells.

As the skilled person will appreciate, methods of producing a population of cells of the invention can be performed using standard techniques in the art.

In an embodiment, the genetic modification is in the genome of the cell.

In an embodiment, the genetic modification is introduced by a programmable nuclease.

In an aspect, the present invention provides a population of cells produced by the method as described herein.

In a further aspect, the present invention provides a population of cells in vitro comprising an exogenous compound which reduces the expression of an antiviral gene and/or reduces the level of antiviral protein activity in the cells when compared to isogenic cells lacking the compound, wherein the cells are capable of producing more virus than a population of the isogenic cells.

In an embodiment, the exogenous compound is a small carbon based molecule, a protein binding agent, a programmable nuclease, a polynucleotide or a combination of two or more thereof.

In an embodiment, the protein binding agent or the polynucleotide is expressed from a transgene administered to the cell.

In an embodiment, the protein binding agent is an antibody.

Any embodiment herein shall be taken to apply mutatis mutandis to any other embodiment unless specifically stated otherwise. For instance, as the skilled person would understand examples of programmable nucleases outlined above for a method of the invention comprising a genetic modification equally apply to the methods of the invention comprising an exogenous compound.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANING DRAWINGS

FIG. 1. Antiviral activity of recombinant chicken (rch) IFN$\alpha$, IFN$\beta$, IFN$\gamma$ and IFN$\lambda$ in a virus neutralization assay. An increase in cell viability equates to an increase in the OD. Absorbance values are the means±SE, duplicates from two independent experiments. Cells alone and cells+virus controls are shown as the means from 24 wells.

Figure 2:
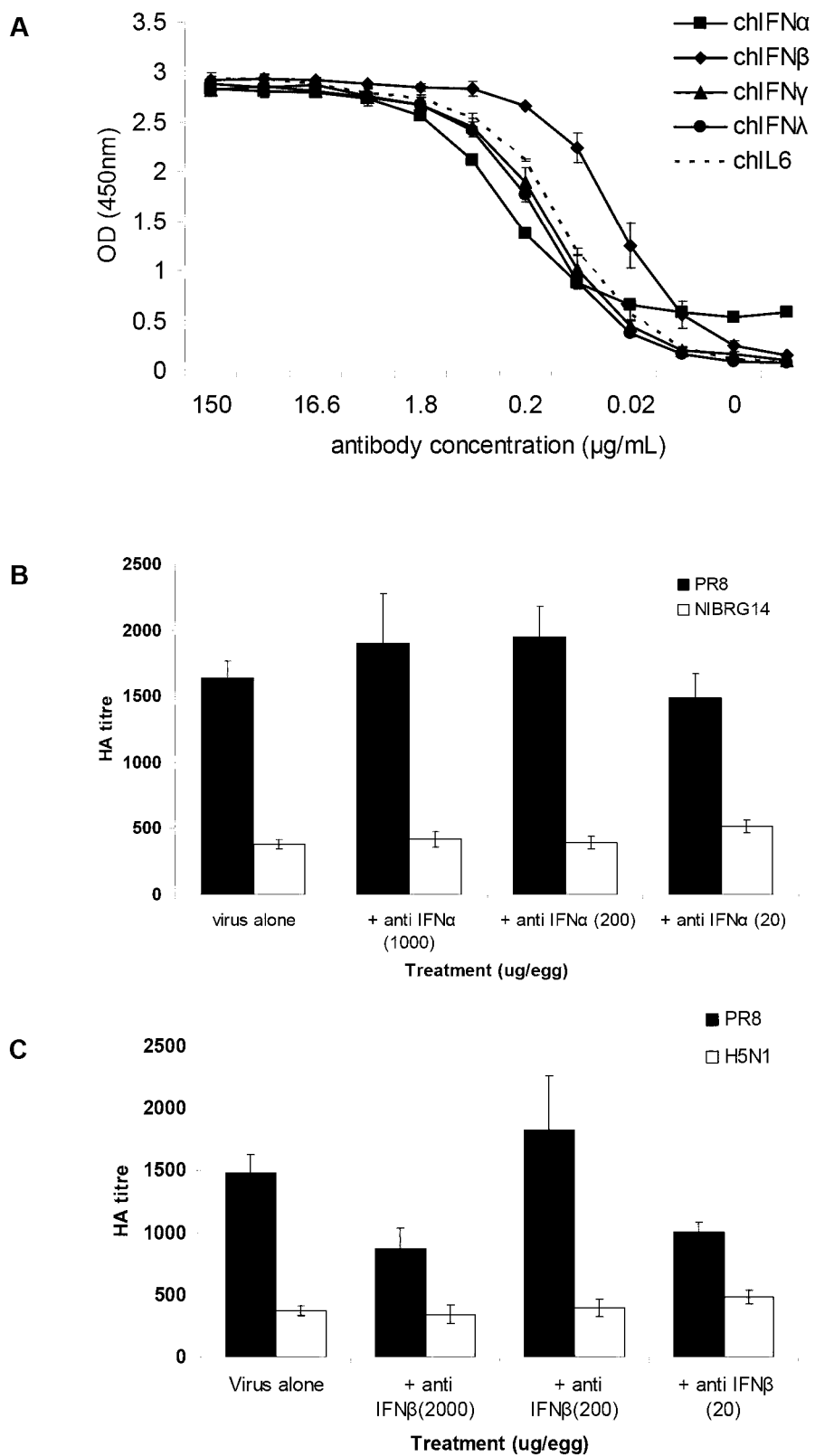

FIG. 2. A. Indirect ELISA analysis reveals that purified anti-IFNs (IFN$\alpha$, IFN$\beta$, IFN$\gamma$ and IFN$\lambda$) sera recognise homologous protein. The graph shows that ammonium sulphate precipitated polyclonal anti-chIFN antisera detects homologous proteins in ELISA. The OD is a measure of antibody levels. Absorbance values shown are the means±SE, duplicates from two independent experiments. B. Anti-chIFN-$\alpha$ antibodies do not appear to increase virus titre in ovo. Anti-chIFN-$\alpha$ antibodies co-inoculated with influenza vaccine virus (PR8 or NIBRG14) in ovo do not augment the haemagglutination (HA) titre measured by haemagglutination (HA) assay. The bar graph represents the mean of four experiments±SE. C. Anti-chIFN-$\beta$ antibodies do not appear to increase virus titre in ovo. The co-administration of purified anti-chIFN-$\beta$ antibodies and influenza vaccine virus (PR8 or NIBRG14) does not affect the virus HA titres in ovo determined by HA assay. The bar graph represents the mean of up to three experiments±SE.

Figure 3:
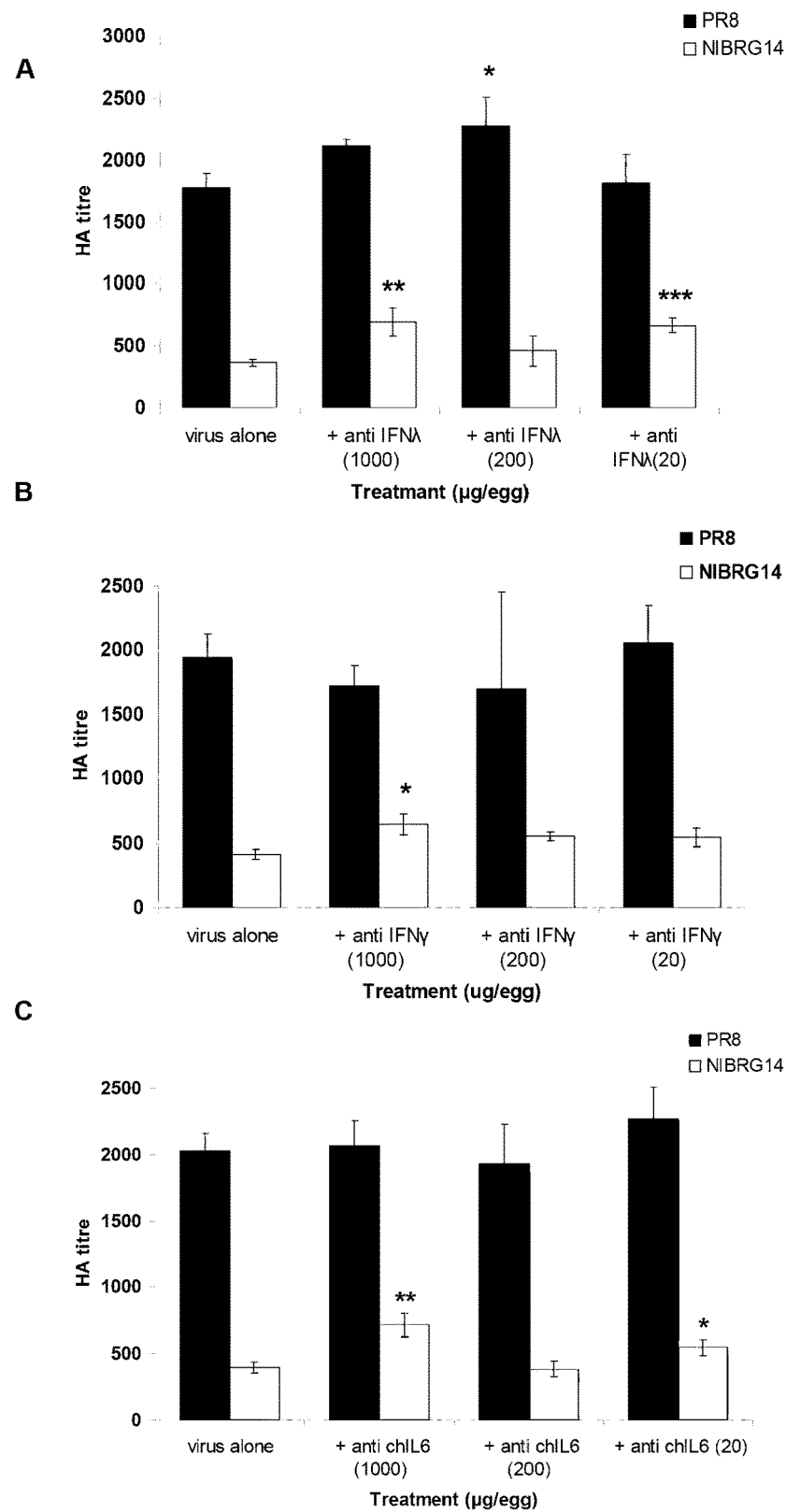

FIG. 3. A. Anti-chIFN-$\lambda$ antibodies increase virus titre in ovo. The inoculation of purified anti-chIFN-$\lambda$ antibodies and influenza vaccine virus (PR8 or NIBRG14) results in an increased HA titre in ovo measured by HA assay. The bar graph represents the means of up to seven experiments±SE. The statistical significance is represented as one asterisk (*) $p<0.05$, two asterisks () $p<0.005$ and three asterisks (*) represents $p=0.0001$. B. Anti-chIFN-$\gamma$ antibodies increase virus titre in ovo. The co-administration of anti-chIFN-$\gamma$ antibodies and influenza vaccine virus (PR8 or NIBRG14) results in an increase on the virus HA titre in ovo measured by HA assay. The bar graph represents the means of 2 experiments±SE. The statistical significance is represented as one asterisk (*) $p<0.05$. C. Anti-chIL-6 antibodies increase virus titre in ovo. The effect of injecting both purified anti-chIL-6 antibodies and influenza vaccine virus (PR8 or NIBRG14) in ovo results in an increase in the HA virus titre measured by HA assay. The bar graph represents the mean of up to five experiments±SE. The statistical significance is represented as one asterisk (*) p<0.05, two asterisks (**) p<0.005.

Figure 4:
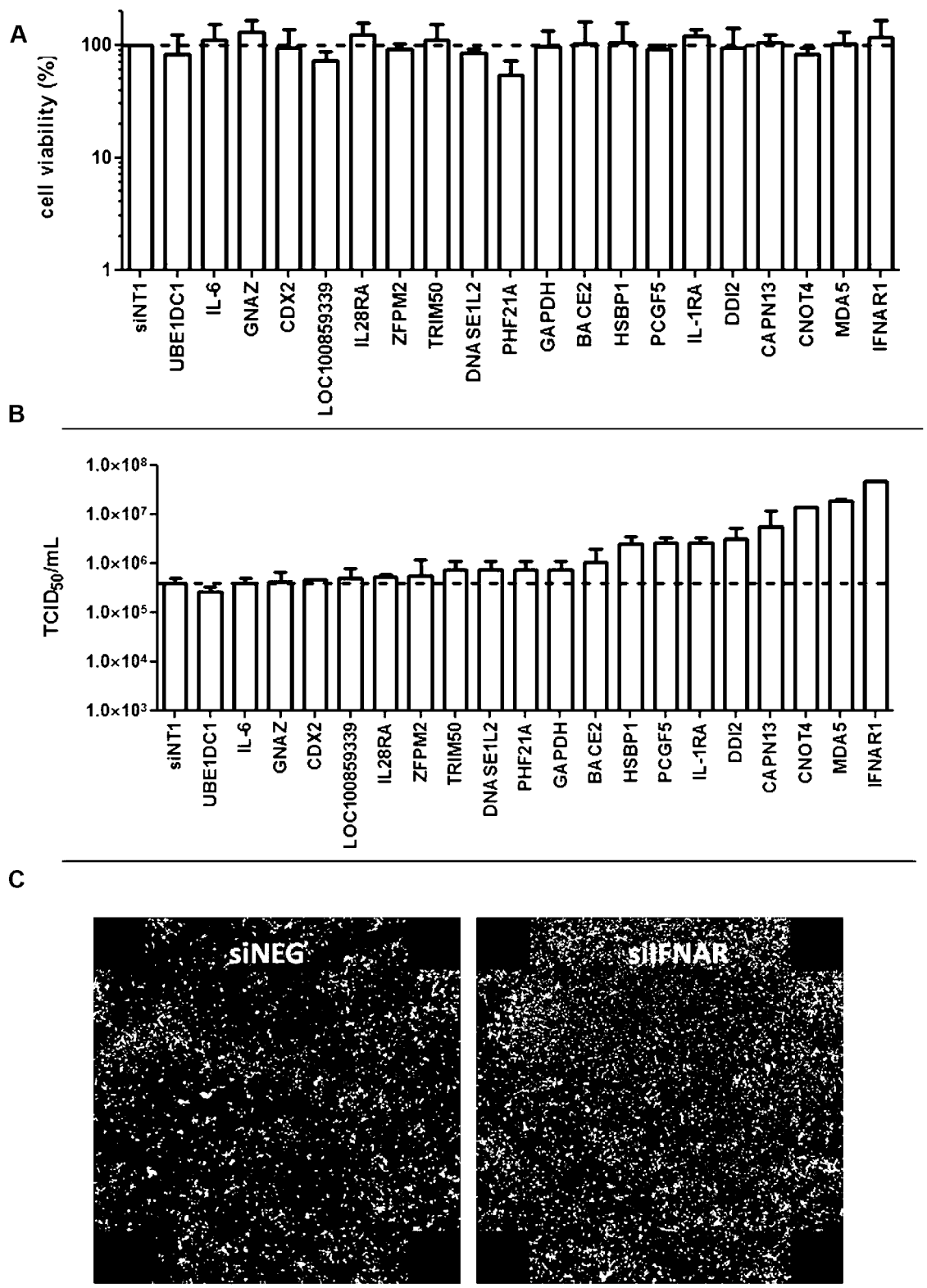

FIG. 4. Screening and identification of antiviral genes for vaccine production of avian influenza. A. Viability of DF-1 cells transfected with a negative control siRNA (siNT1), or with siRNAs targeting the 21 candidate host genes. Viability was measured 72 h post transfection, at the time of virus infection. B. Titres of influenza A/WSN grown in the immortalized chicken fibroblast cell line, DF-1, in control cells (siNT1), or in cells transfected with siRNAs to silence expression of 21 host genes. A significant increase in viral titres measured as $TCDI_{50}$ after KD using siRNA was observed, with IFNRA1 shows the highest increase in viral titre. C. Immune staining of viral particles on DF1 cells show a significant increase in virus growth after inhibition of IFNAR1 expression by siRNA.

Figure 5:
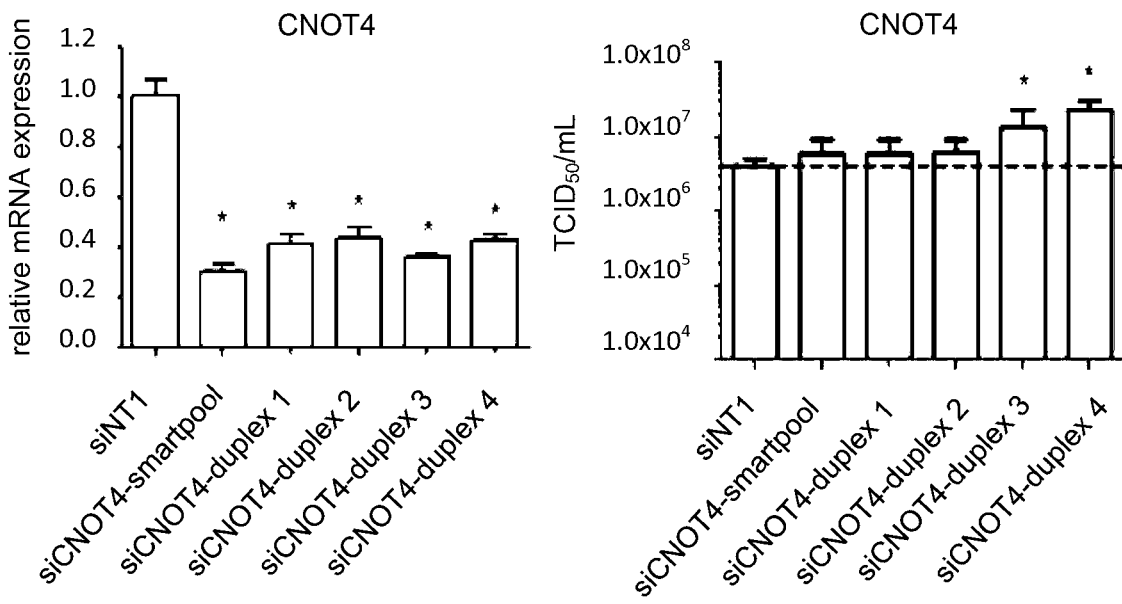
Figure 5:
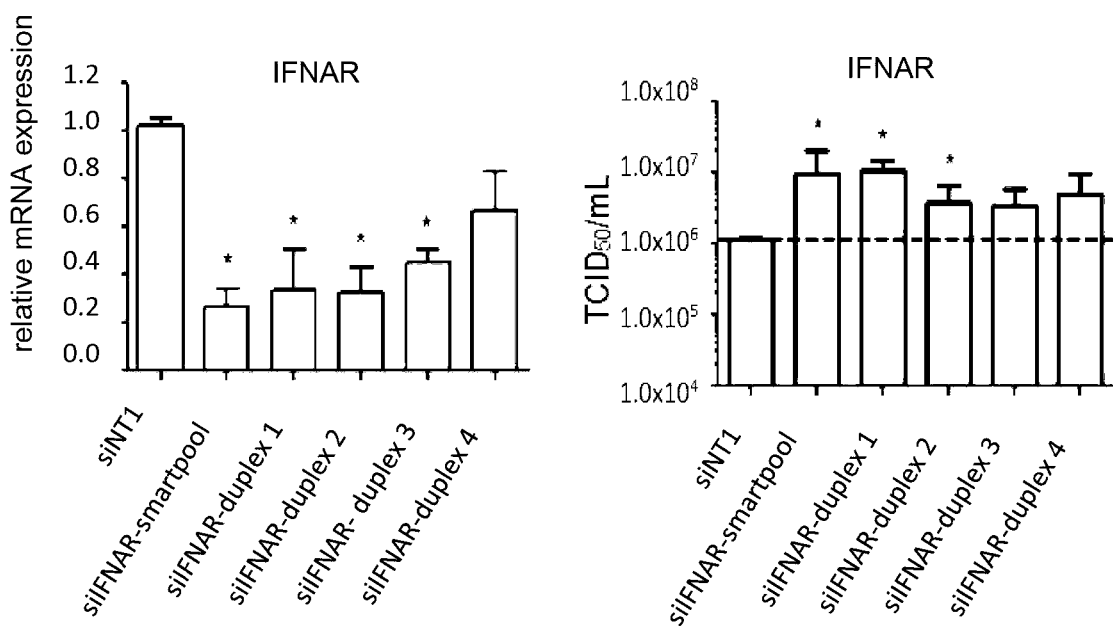
Figure 5:
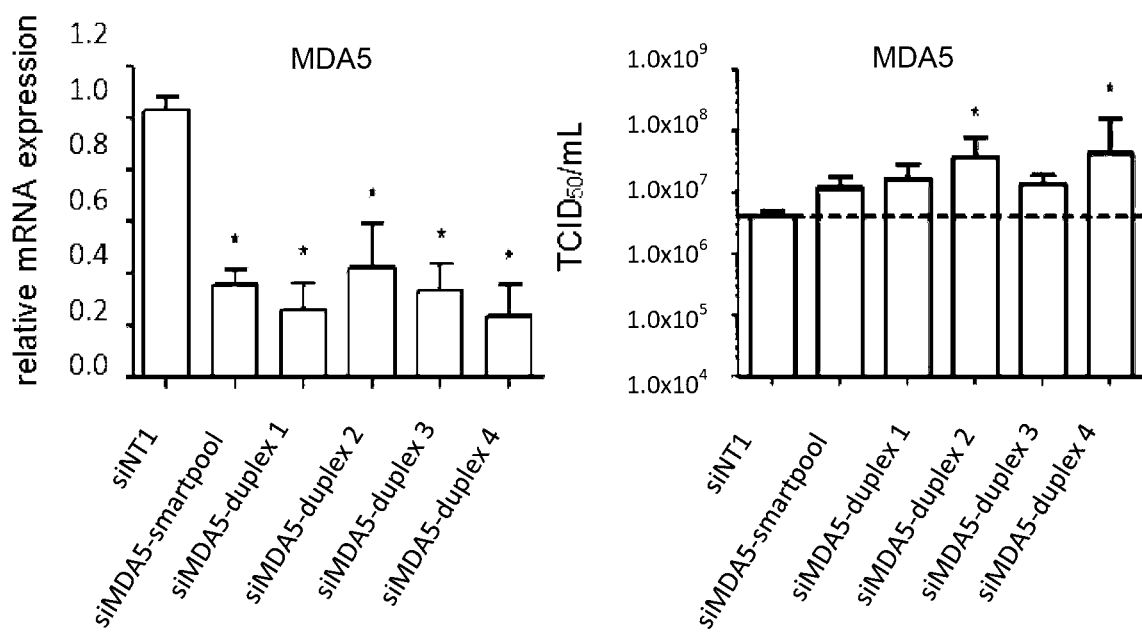
Figure 5:
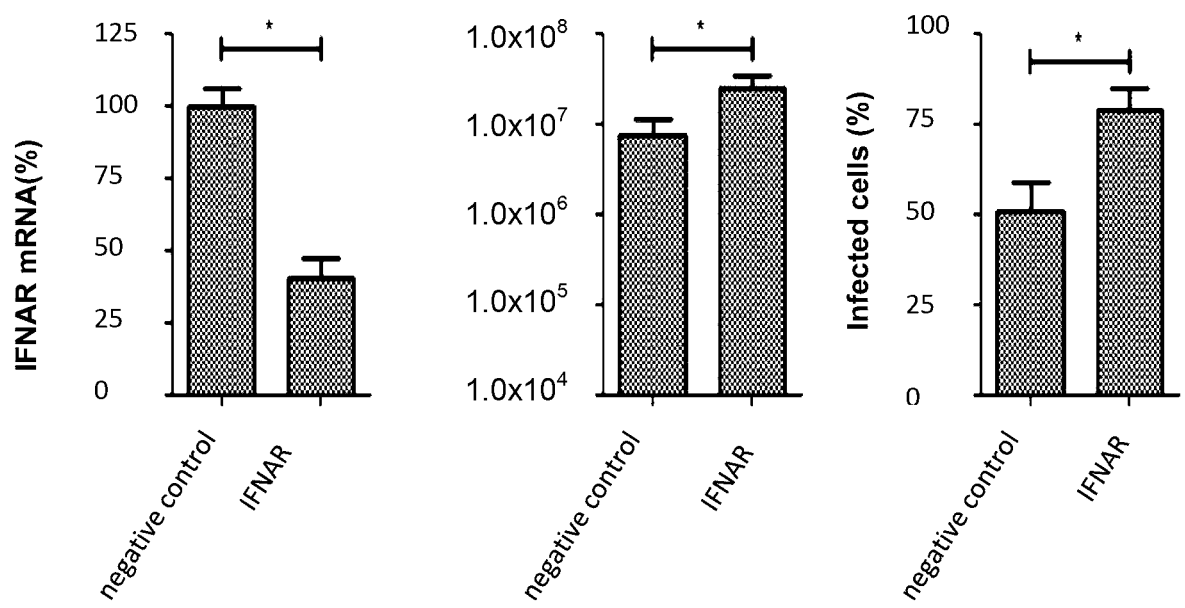

FIG. 5. siRNA down regulation of gene expression of the host increases viral growth in vitro. DF-1 cells were transfected with a negative control siRNA (siNT1), or siRNAs targeting CNOT4, IFNAR or MDA5, either as 4 siRNA duplexes pooled (smartpool), or as individual siRNA duplexes. *$p<0.05$ compared to mRNA levels in cells transfected with siNT1. mRNA levels were quantitated using Taqman probes 72 h post-transfection by quantitative real-time PCR. Each of the siRNA complexes were evaluated individually on its ability to KD the target gene (shown on the left) and increase viral titres (show on the right). Cells were infected with influenza A/WSN virus (MOI 0.1) for 48 h. Virus levels in the cell supernatant were quantitated by $TCID_{50}$ assays. *$p<0.05$ compared to virus levels in cells transfected with siNT1.

Figure 6:
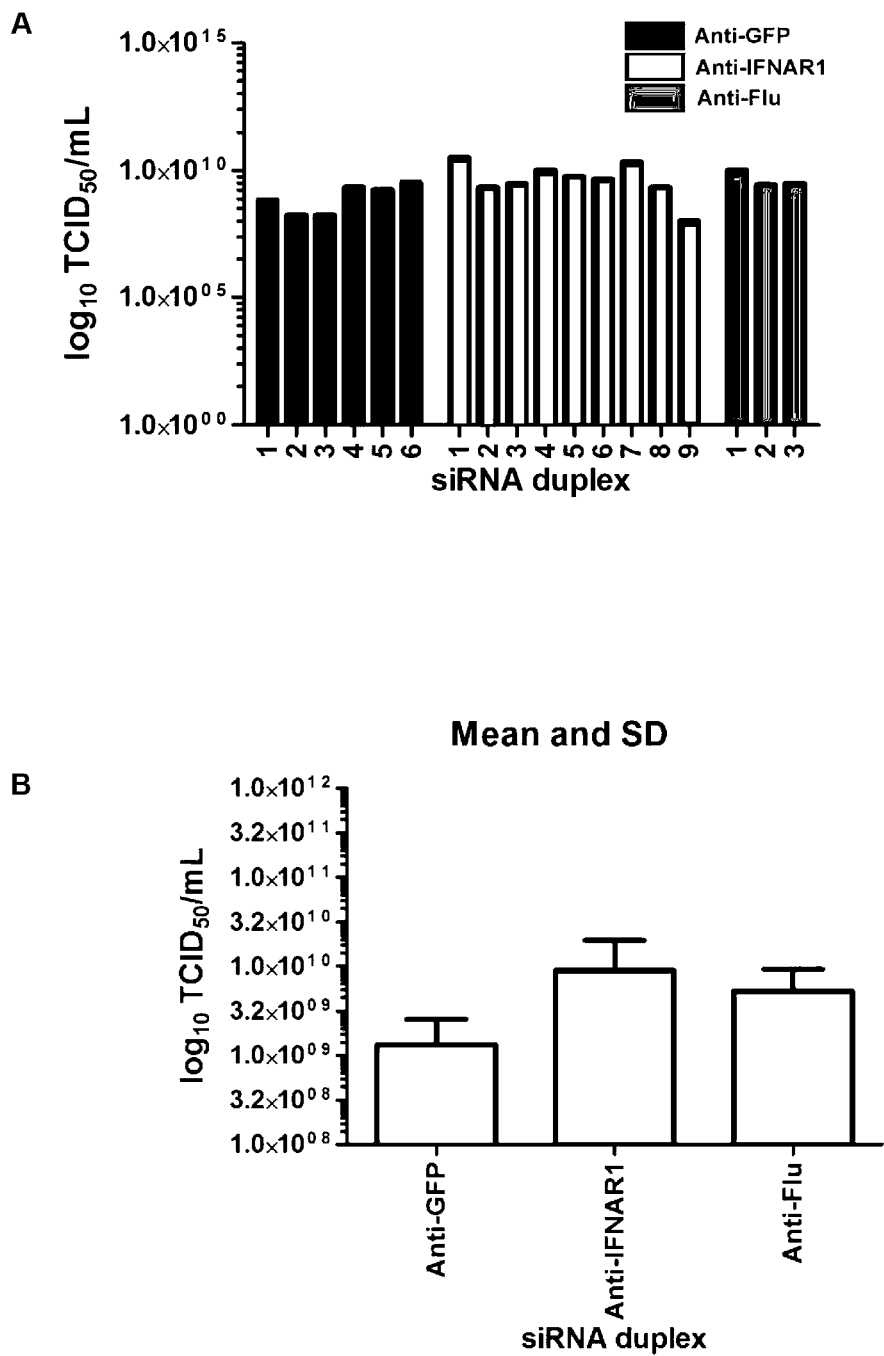

FIG. 6. $TCID_{50}$ WSN from eggs. A. $TCID_{50}$ WSN from eggs after down regulation by siRNA delivered using ABA-21/117Q values are given as a single replicates. B. $TCID_{50}$ WSN from eggs after down regulation by siRNA delivered using ABA-21/117Q. Values are given as Mean+2 SD.

Figure 7:
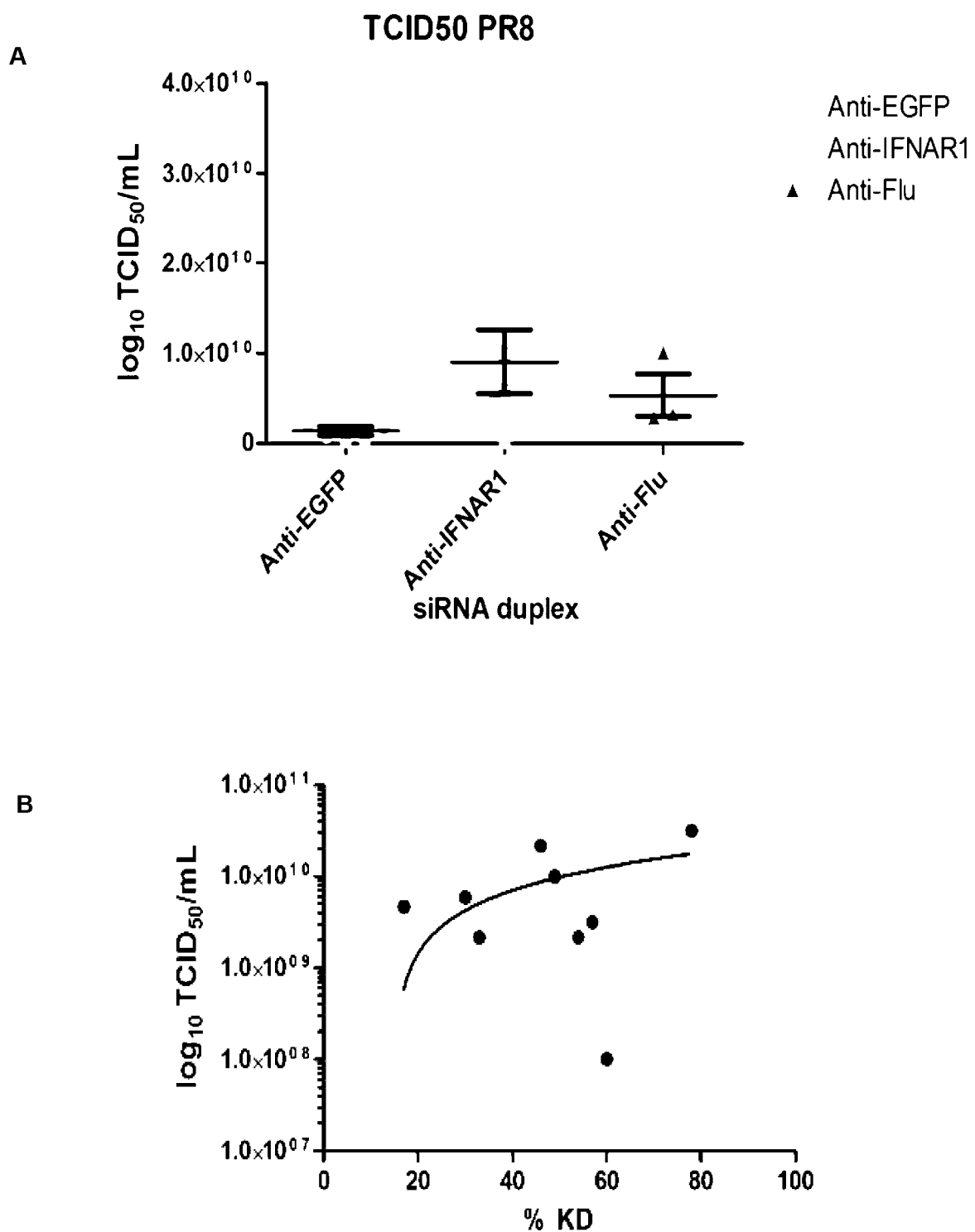
Figure 7:
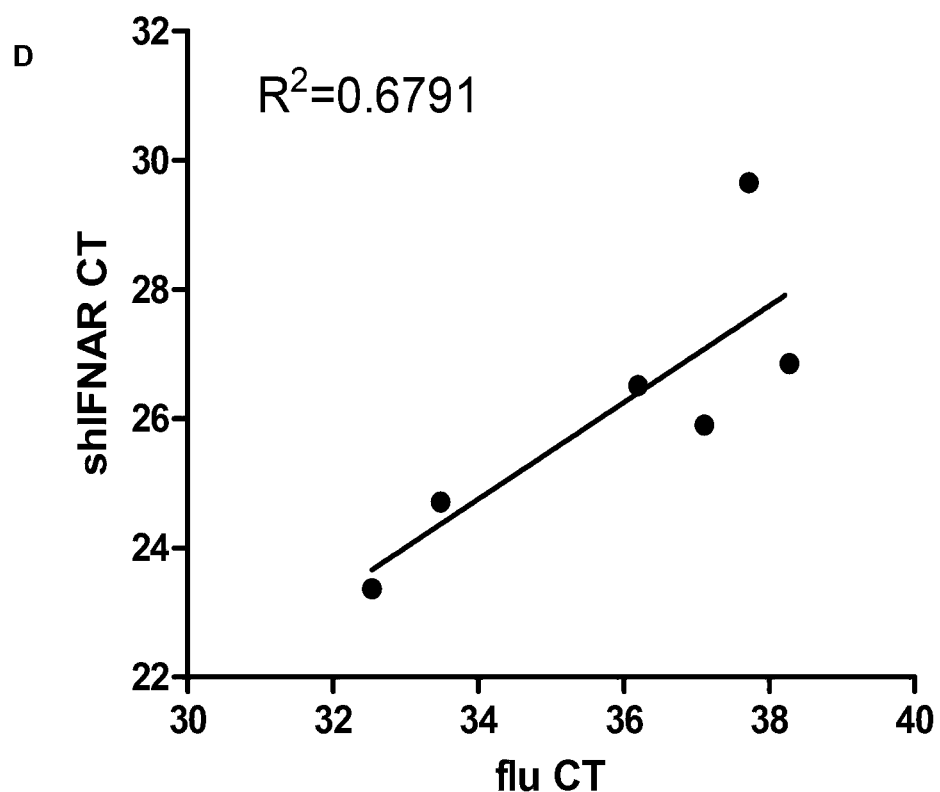

FIG. 7. $TCID_{50}$ WSN from eggs. A. $TCID_{50}$ PR8 vaccine strain from eggs after down regulation by siRNA delivered using ABA-21/117Q. Values are given as Mean+2SD. B. Correlation between $TCID_{50}$ titre and knockdown of IFNAR1. C. HA and $TCID_{50}$ maximum values obtained by down regulation by siRNA delivered using ABA-21/117Q it correspond to a 3 log increase compared with control. shIFNAR1 increases influenza growth in eggs. D. Expression of shIFNAR1 and levels of influenza RNA were measured in the heart of day 12 embryos following injection of RCAS-shIFNA1 at day 0 and infection with influenza (PR8 strain) at day 10 of embryogenesis. The raw CT values from the real-time PCR shows a correlation between the expression of shIFNAR1 and influenza RNA levels. The higher the expression of shIFNAR1 and influenza RNA is indicated by a lower CT value (N=6).

Figure 8:
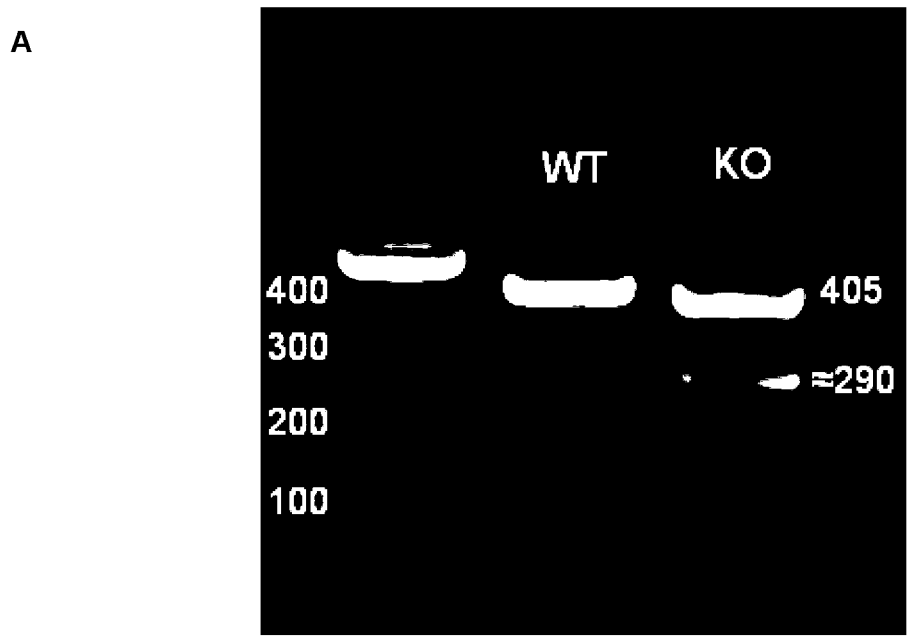
Figure 8:
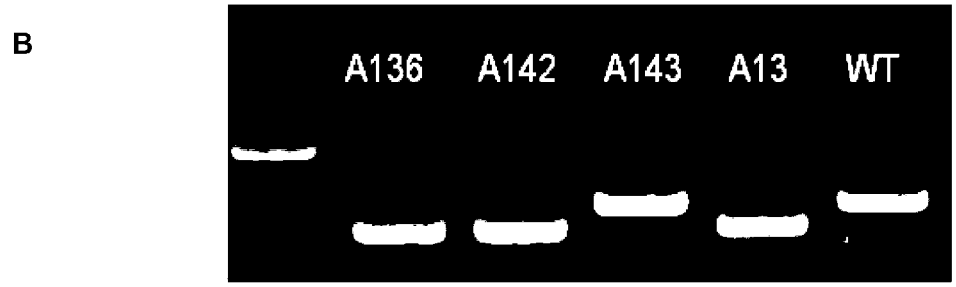
Figure 8:
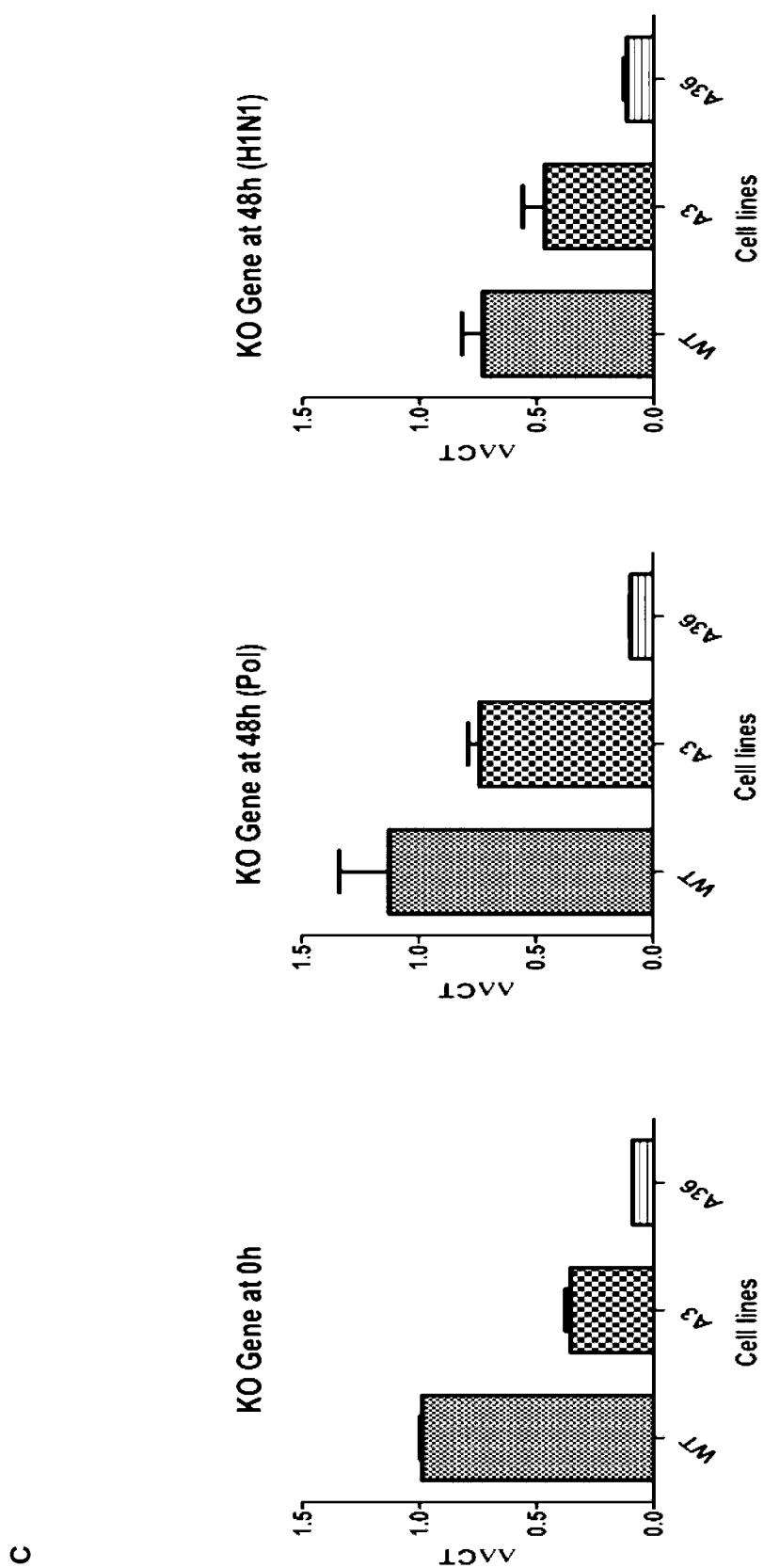
Figure 8:
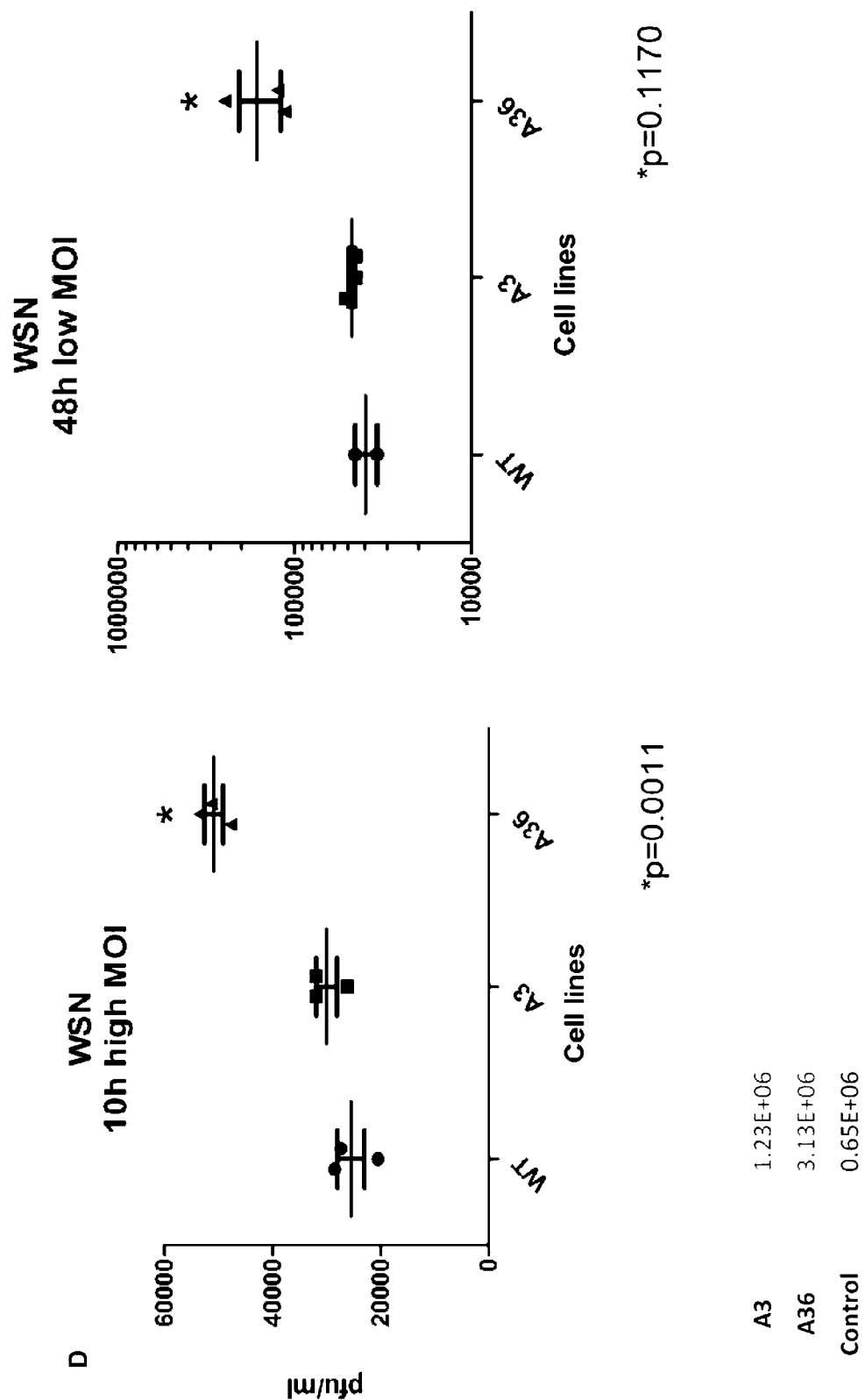

FIG. 8. Generation of IFNAR1 DF-1 KO cell lines. After transfection, the cells from the parental cell lines presented an alternative amplicon during the PCR screening in around 30% of the alleles. A. Deletion was confirmed by sequencing. Cells were sorted to obtain single clones presenting: biallelic (A136 and A142) mono-allelic (A13) or no apparent deletion (A143) when compared with the Wild Type (WT). B. IFNAR1A gene expression was evaluated by qPCR. Results expressed as the mean of ΔΔct value +/−2 standard deviation (SD) against housekeeping WSN viral particles produced on the KO cell lines. Pfu and $TCID_{50}$ were establish after infecting MDCK cells with the H1N1 A/WSN/1933 growth on the different cell lines as an indicative of total virus yield. C. Gene KO at 0 and 48 h. D. WSN viral particles produced on the KO cell lines. Pfu and $TCID_{50}$ were establish after infecting MDCK cells with the H1N1 A/WSN/1933 growth on the different cell lines as an indicative of total virus yield.

Figure 9:
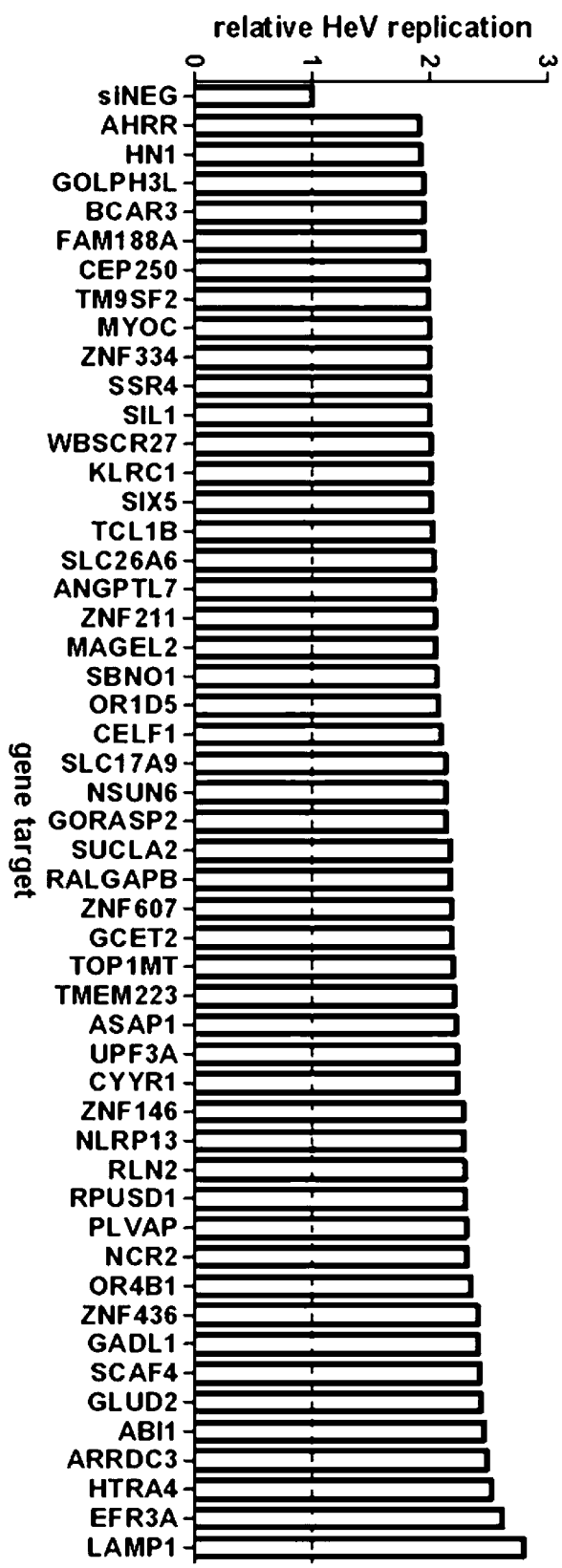

FIG. 9. Screening and identification of antiviral genes against Hendra Virus. Hendra virus replication in the immortalized human cell line HeLa, in control cells (siNT1), or in cells transfected with siRNAs to silence expression listed. A significant increase in viral replication using siRNA was observed. LAMP1 shown the highest increase in viral titre.

DETAILED DESCRIPTION OF THE INVENTION

General Techniques and Selected Definitions

Unless specifically defined otherwise, all technical and scientific terms used herein shall be taken to have the same meaning as commonly understood by one of ordinary skill in the art (e.g., in cell culture, molecular genetics, immunology, immunohistochemistry, precision genome engineering, protein chemistry, and biochemistry).

Unless otherwise indicated, the cell culture and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein, the term "replicating a virus" refers to increasing the number of copies of a virus in a cell and/or medium compared to the starting copy number of a virus in the cell and/or medium using the host cells replication machinery.

As used herein, the term "population of cells" is any population of cells that can be cultured in vitro using cell culture methods and in which a virus can replicate. In an embodiment, the cells can be mammalian, avian or Arthropoda. In an embodiment, the cells are from a primary cell line. In an embodiment, the cells are from an immortalized cell line. In an embodiment, the cells are adherent cells. In an embodiment, the cells are non-adherent cells (suspension cells).

As used herein, the term "genetic modification" is any man made alteration to the genetic material of a cell. The modification may have been made to an ancestor of the population of cells or to the population of cells. In one example, the genetic modification is in at least 10%, at least 20%, at least 30%, at least 40%, at least 50%, at least 60%, at least 70%, at least 80%, at least 85%, at least 90%, at least 95% or 100% of the population of cells. In one example, the genetic modification is a mutation to an endogenous gene in the genome introduced by a programmable nuclease. For instance, the mutation can be a frame-shift and/or deletion that results in the gene no longer encoding a functional protein. In another embodiment, homologous recombination is used to delete part of all of a target antiviral gene such that the antiviral protein is not produced. In an alternate embodiment, the genetic modification is the instruction of a transgene, for example in a nucleic acid construct, which expresses the desired polynucleotide in the population of cells. The genetic modification may be extrachromosomal or integrated into the nuclear or mitochondrial genome of the population of cells. In one example, the genetic modification is introduced into the cells before they are isolated from a host. In one example, the genetic modification is introduced in the cells after they have been isolated from a host.

As used herein, the "exogenous compound" can be any substance, such as a small carbon based molecule, protein or polynucleotide, administered to the cell to produce the desired result.

As used herein, the term "producing more virus than a population of the isogenic cells" or similar refers to the ability of the population of cells to be used to cultivate more virus than a population of isogenic cells lacking the genetic modification or exogenous compound as herein described. The isogenic cells are genetically identical to the population of cells of the invention apart from the presence of the genetic modification and/or exogenous compound. In an embodiment, the population of cells of the invention produces at least 0.5 fold, or at least 1 fold, or at least 2 fold, or at least a 3 fold, or at least 5 fold, or at least 10 fold, or at least 15 fold, or at least 20 fold, or at least 50 fold, or at least 100 fold more virus when compared to a population of isogenic cells lacking the genetic modification and/or exogenous compound. Such an increase in virus production can readily be determined by the skilled person using routine techniques. For example, a population of cells having the genetic modification or being administered an exogenous compound can be inoculated with the same amount of the same virus and incubated under the same conditions for the same length of time and the amount of virus particles present in population of cells can be determined using standard techniques, such as those outlined in the Examples.

As used herein, the term "virus or particles thereof" refers to whole virus which may or may not be inactivated and to particles of such viruses. A virus particle can be any size suitable for use in a split virus vaccine or subunit virus vaccine. The whole virus or particles of the virus can be harvested form the populations of cells or the secretions thereof (the supernatant). A harvested whole virus may be disrupted during the preparation of a vaccine composition to form particles of a suitable size for a split virus vaccine or subunit virus vaccine.

As used herein, the term "reduces the expression of an antiviral gene" refers to the ability of the genetic modification and/or exogenous compound to down-regulate the level of RNA transcript and/or the level of translation from the RNA transcript in the a population of cells compared to the level(s) in isogenic cells lacking the genetic modification or exogenous compound. The isogenic cells are genetically identical to the population of cells of the invention apart from the presence of the genetic modification and/or exogenous compound. In an embodiment, the genetic modification and/or exogenous compound reduces expression of the antiviral gene in the population of cells by at least 10%, or at least 20%, or at least 30%, or at least 40%, or at least 50%, or at least 60%, or at least 70%, or at least 80%, or at least 90%, or at least 95%, or at least 98%, or at least 99%, or 100% when compared to isogenic cells lacking the genetic modification and/or exogenous compound. Such a reduction can be identified using standard procedures.

As used herein, the term "reduces the level of antiviral protein activity" refers to the ability of the genetic modification and/or exogenous compound to down-regulate the level antiviral protein activity in the population of cells when compared to the level in isogenic cells lacking the genetic modification. In an embodiment, the isogenic cells are genetically identical to the population of cells of the invention apart from the presence of the genetic modification and/or exogenous compound. The activity of the protein can be reduced by, for example, reducing the amount of the protein in the population of cells and/or reducing the ability of the protein to perform its natural function in the population of cells (such as by binding an exogenous compound (for example an antibody) to its active site). In an embodiment, the genetic modification and/or exogenous compound reduces the level of antiviral protein activity in the population of cells by at least 10%, or at least 20%, or at least 30%, or at least 40%, or at least 50%, or at least 60%, or at least 70%, or at least 80%, or at least 90%, or at least 95%, or at least 98%, or at least 99%, or 100% when compared to isogenic cells lacking the genetic modification and/or exogenous compound. Such a reduction can be identified using standard procedures.

A "transgene" as referred to herein has the normal meaning in the art of biotechnology and includes a genetic sequence which has been produced or altered by recombinant DNA or RNA technology and which has been introduced into the population of cells of the present invention. Typically, the transgene has been introduced into the population of cells of the present invention, by transformation but any method can be used as one of skill in the art recognizes. A transgene includes genetic sequences that are introduced into a chromosome as well as those that are extrachromosomal. The transgene will typically comprise an open reading frame encoding a polynucleotide of interest operably linked to a suitable promoter for expressing the polynucleotide in the population of cells of the present invention.

The term "small carbon based molecule," as used herein, refers to a chemical compound or molecule having a molecular weight below 2000 Daltons, preferably below 1500 Daltons, more preferably below 1000 Daltons, still more preferably below 750 Daltons, yet more preferably below 500 Daltons.

The term "avian" as used herein refers to any species, subspecies or race of organism of the taxonomic Class Aves, such as, but not limited to, such organisms as chicken, turkey, duck, goose, quail, pheasants, parrots, finches, hawks, crows and ratites including ostrich, emu and cassowary. The term includes the various known strains of Gallus gallus (chickens), for example, White Leghorn, Brown Leghorn, Barred-Rock, Sussex, New Hampshire, Rhode Island, Australorp, Cornish, Minorca, Amrox, California Gray, Italian Partidge-coloured, as well as strains of turkeys, pheasants, quails, duck, game hen, guinea fowl, squab, ostriches and other poultry commonly bred in commercial quantities.

Antiviral Genes and/or Proteins

As used herein, an "antiviral gene" is any gene endogenous to the population of cells, the expression of which limits the production of the virus in the population of cells by any means. An antiviral gene may encode an antiviral protein.

As used herein, an "antiviral protein" is any protein endogenous to the population of cells, the presence of which limits the production of the virus in the population of cells.

The antiviral gene and/or protein may be involved in the ability of a cell to mount a response to a viral infection. In an embodiment, the antiviral gene and/or protein forms part of an interferon (IFN) pathway. In an embodiment, the antiviral gene and/or protein is in the Type I, Type II or Type III interferon pathway. In an embodiment, the antiviral gene and/or protein is in the Type I or Type III interferon pathway. In an embodiment, the antiviral gene and/or protein is the IFN-α/β receptor1 (IFNAR1) chain. In another embodiment, the antiviral gene and/or protein is IL-6.

In an alternate embodiment, the antiviral gene and/or protein may be, or known to be, involved in the ability of a cell to mount an immune response to a viral infection. Examples of some previously known functions of such genes/proteins include being involved in cellular metabolism, embryonic development, cell signalling or nucleic acid synthesis.

In an alternate embodiment, reducing the expression of the antiviral gene and/or protein reduces apoptosis of cells infected with the virus.

In an embodiment, the antiviral gene and/or protein is selected from one, two, three, four or more of: DDI2, HSBP1, GNAZ, NPR2, CNOT4, MDA5, IFNα, IL-6, IFNAR1, IFNβ, IFNγ, IFNλ, UBE1DC1, CDX2, LOC100859339, IL28RA, ZFPM2, TRIM50, DNASEIL2, PHF21A, GAPDH, BACE2, PCGF5, IL-1RA, CAPN13, UBA5, IFIH1, LAMP1, EFR3A, ARRDC3, ABI1, SCAF4, GADL1, ZKSCAN7, PLVAP, RPUSD1, CYYR1, UPF3A, ASAP1, NXF1, TOP1MT, RALGAPB, SUCLA2, GORASP2, NSUN6, CELF1, ANGPTL7, SLC26A6, WBSCR27, SILL, HTT, MYOC, TM9SF2,CEP250, FAM188A, BCAR3, GOLPH3L, HN1, ADCY7, AKAP10, ALX1, CBLN4, CRK, CXORF56, DDX10, EIF2S3, ESF1, GBF1, GCOM1, GTPBP4, HOXB9, IFT43, IMP4, ISY1, KIAA0586, KPNA3, LRRIQ1, LUC7L, MECR, MRPL12, POLR3E, PWP2, RPL7A, SERPINH1, SLC47A2, SMYD2, STAB1, TTK, WNT3, XPO1, AHHR, ZNF334, SSR4, KLRC1, SIX5, TCL1B, ZNF211, MAGEL2, SBN01, OR1D5, SLC17A9, ZNF607, GCET2, TMEM223, ZNF146, NLRP13, RLN2, NCR2, OR4B1, GLUD2, IFNAR2, IFNGR1, INFGR2, IL-10R2, IFNκ, IFNΩ, IL-1RB and HTRA4 or the corresponding receptor or agonist thereof. In an embodiment, IFNα is one or more of the following isoforms: IFNα1, IFNα2, IFNα4, IFNα5, IFNα6, IFNα7, IFNA8, IFNα10, IFNα13, IFNα14, IFNα16, IFNα17 and IFNα21. In an embodiment, IFNλ is one or more of the following isoforms: IFNλ1, IFNλ2, IFNλ3, IFNλ4.

In an embodiment, the antiviral gene and/or protein is selected from one, two, three, four or more of: DDI2, HSBP1, GNAZ, NPR2, CNOT4, MDA5, IFNα, IL-6, IFNAR1, IFNβ, IFNγ, IFNλ, UBE1DC1, CDX2, LOC100859339, IL28RA, ZFPM2, TRIM50, DNASEIL2, PHF21A, GAPDH, BACE2, PCGF5, IL-1RA, CAPN13, UBA5, IFIH1, LAMP1, EFR3A, ARRDC3, ABI1, SCAF4, GADL1, ZKSCAN7, PLVAP, RPUSD1, CYYR1, UPF3A, ASAP1, NXF1, TOP1MT, RALGAPB, SUCLA2, GORASP2, NSUN6, CELF1, ANGPTL7, SLC26A6, WBSCR27, SILL, HTT, MYOC, TM9SF2,CEP250, FAM188A, BCAR3, GOLPH3L, HN1, ADCY7, AKAP10, ALX1, CBLN4, CRK, CXORF56, DDX10, EIF2S3, ESF1, GBF1, GCOM1, GTPBP4, HOXB9, IFT43, IMP4, ISY1, KIAA0586, KPNA3, LRRIQ1, LUC7L, MECR, MRPL12, POLR3E, PWP2, RPL7A, SERPINH1, SLC47A2, SMYD2, STAB1, TTK, WNT3, XPO1, AHHR, ZNF334, SSR4, KLRC1, SIX5, TCL1B, ZNF211, MAGEL2, SBN01, OR1D5, SLC17A9, ZNF607, GCET2, TMEM223, ZNF146, NLRP13, RLN2, NCR2, OR4B1, GLUD2 and HTRA4 or the corresponding receptor or agonist thereof.

In an embodiment, the antiviral gene and/or protein is selected from one, two, three, four or more of: DDI2, HSBP1, GNAZ, NPR2, CNOT4, MDA5, IFNα, IL-6, UBE1DC1, CDX2, LOC100859339, IL28RA, ZFPM2, TRIM50, DNASEIL2, PHF21A, GAPDH, BACE2, PCGF5, IL-1RA, CAPN13, UBA5, IFIH1, LAMP1, EFR3A, ARRDC3, ABI1, SCAF4, GADL1, ZKSCAN7, PLVAP, RPUSD1, CYYR1, UPF3A, ASAP1, NXF1, TOP1MT, RALGAPB, SUCLA2, GORASP2, NSUN6, CELF1, ANGPTL7, SLC26A6, WBSCR27, SIL1, HTT, MYOC, TM9SF2,CEP250, FAM188A, BCAR3, GOLPH3L, HN1, ADCY7, AKAP10, ALX1, CBLN4, CRK, CXORF56, DDX10, EIF2S3, ESF1, GBF1, GCOM1, GTPBP4, HOXB9, IFT43, IMP4, ISY1, KIAA0586, KPNA3, LRRIQ1, LUC7L, MECR, MRPL12, POLR3E, PWP2, RPL7A, SERPINH1, SLC47A2, SMYD2, STAB1, TTK, WNT3, XPO1, AHHR, ZNF334, SSR4, KLRC1, SIX5, TCL1B, ZNF211, MAGEL2, SBN01, OR1D5, SLC17A9, ZNF607, GCET2, TMEM223, ZNF146, NLRP13, RLN2, NCR2, OR4B1, GLUD2 and HTRA4 or the corresponding receptor or agonist thereof.

In an embodiment, the antiviral gene and/or protein is selected from one, two, three, four or all of: DDI2, HSBP1, GNAZ, NPR2, CNOT4, MDA5, IFNα, IL-6, IFNAR1, IFNβ, IFNγ, IFNλ.

In an embodiment, the antiviral gene and/or protein is MDA5. In an embodiment, the antiviral gene and/or protein is IL-6. In an embodiment, the antiviral gene and/or protein is CNOT4. In another embodiment, the antiviral gene and/or protein is IFNα. In an embodiment, the antiviral gene and/or protein is DDI2. In an embodiment, the antiviral gene and/or protein is HSBP1. In an embodiment, the antiviral gene and/or protein is GNAZ. In an embodiment, the antiviral gene and/or protein is NPR2.

In an embodiment, the antiviral gene and/or protein is selected from one, two, three or all of: AHHR, ZNF334, SSR4, KLRC1, SIX5, TCL1B, ZNF211, MAGEL2, SBN01, OR1D5, SLC17A9, ZNF607, GCET2, TMEM223, ZNF146, NLRP13, RLN2, NCR2, OR4B1, GLUD2 and HTRA4. In an embodiment, the antiviral gene and/or protein is selected from one, two, three or all of: AHHR, ZNF334, SSR4, KLRC1, SIX5, TCL1B, ZNF211, MAGEL2, SBN01, OR1D5, SLC17A9, ZNF607, GCET2, TMEM223, ZNF146, NLRP13, RLN2, NCR2, OR4B1, GLUD2 and HTRA4 and the population of cells are mammalian cells. In an embodiment, the antiviral gene and/or protein is selected from one, two, three or all of: AHHR, ZNF334, SSR4, KLRC1, SIX5, TCL1B, ZNF211, MAGEL2, SBN01, OR1D5, SLC17A9, ZNF607, GCET2, TMEM223, ZNF146, NLRP13, RLN2, NCR2, OR4B1, GLUD2 and HTRA4, the population of cells are mammalian cells and the virus is the Hendra virus.

Further details regarding the antiviral genes and/or proteins that can be targeted is provided below in Table 1.

TABLE 1

| Gene | Name | GENE ID | Ref SeqID mRNA | Pathway |
|---|---|---|---|---|
| | Antiviral genes and/or proteins | | | |
| CDX2 | caudal type homeobox 2 | 374205 | NM_204311 | Nucleic acid synthesis |
| HSBP1 | heat shock factor binding protein 1 | 415813 | NM_001112809 | Embryo development |
| GAPDH | glyceraldehyde-3-phosphate dehydrogenase | 374193 | NM_204305 | Metabolism |
| ARRDC3 | arrestin domain containing 3 | 427107 | XM_424699.3 | Metabolism |
| SCAF4 | SR-related CTD-associated factor 4 | 418492 | NM_001012822.1 | Nucleic acid synthesis |
| RPUSD1 | RNA pseudouridylate synthase domain containing 1 | 771031 | XM_004945221.1 | Nucleic acid synthesis |
| UPF3A | UPF3 regulator of nonsense transcripts homolog A | 418734 | XM_416933.4 | Metabolism |
| TOP1MT | topoisomerase (DNA) I, mitochondrial | 408025 | NM_001001300.1 | Metabolism |
| RALGAPB | Ral GTPase activating protein, beta subunit | 419128 | NM_001030846.1 | Cell signalling |
| SUCLA2 | succinate-CoA ligase, ADP-forming, beta subunit | 418857 | NM_001006271.2 | Embryo development |
| GORASP2 | Golgi reassembly stacking protein 2, 55 kDa | 424156 | NM_001012594.1 | Immune response |
| CELF1 | CUGBP, Elav-like family member 1 | 373923 | NM_001012521.1 | Embryo development |
| SLC26A6 | solute carrier family 26 (anion exchanger), member 6 | 416012 | NM_001252254.1 | Metabolism |
| WBSCR27 | Williams Beuren syndrome chromosome region 27 | 770708 | XM_001234037.3 | Embryo development |
| HTT | huntingtin | 422878 | XM_420822.4 | Metabolism |
| MYOC | myocilin, trabecular meshwork inducible glucocorticoid response | 424391 | XM_422235.4 | Metabolism |
| TM9SF2 | transmembrane 9 superfamily member 2 | 418777 | XM_416972.4 | Metabolism |
| CEP250 | centrosomal protein 250 kDa | 419138 | XM_004946945.1 | Nucleic acid synthesis |
| FAM188A | family with sequence similarity 188, member A | 420526 | XM_418629.4 | Nucleic acid synthesis |
| AKAP10 | A kinase (PRKA) anchor protein 10 | 417612 | XM_415856.4 | Cell signalling |
| ALX1 | ALX homeobox 1 | 427871 | XM_425445.4 | Embryo development |
| CRK | v-crk avian sarcoma virus CT10 oncogene homolog | 417553 | L08168.1 | Immune response |
| GBF1 | Golgi brefeldin A resistant guanine nucleotide exchange factor 1 | 423758 | XM_421632.4 | Cell signalling |
| HOXB9 | homeobox B9 | 771865 | XM_001233690.3 | Metabolism |
| IMP4 | U3 small nucleolar ribonucleoprotein | 100857200 | NM_001277715.1 | Nucleic acid synthesis |
| ISY1 | Splicing factor homolog (S. cerevisiae) | 415968 | XM_414311.2 | Nucleic acid synthesis |
| KIAA0586 | Talpid3 | 423540 | NM_001040707.1 | |
| SERPINH1 | serpin peptidase inhibitor, clade H (heat shock protein 47), member 1, (collagen binding protein 1) | 396228 | NM_205291.1 | Metabolism |
| SLC47A2 | solute carrier family 47, member 2 | 417616 | NM_001135679.1 | Metabolism |
| STAB1 | stabilin 1 | 415894 | XM_414246.4 | Embryo development |
| TTK | TTK protein kinase | 421849 | XM_419867.4 | Cell signalling |
| WNT3 | wingless-type MMTV integration site family, member 3 | 374142 | NM_001081696.1 | Cell signalling |
| GNAZ | guanine nucleotide binding protein (G protein), alpha z polypeptide | 770226 | XM_001232444 | Metabolism |

TABLE 1-continued

Antiviral genes and/or proteins

| Gene | Name | GENE ID | Ref SeqID mRNA | Pathway |
|---|---|---|---|---|
| MECR | mitochondrial trans-2-enoyl-CoA reductase | 419601 | XM_417748.4 | Metabolism |
| BACE2 | beta-site APP-cleaving enzyme 2 (BACE2) | 418526 | XM_416735.4 | Metabolism |
| ZFPM2 | zinc finger protein, FOG family member 2 | 420269 | XM_418380 | Nucleic acid synthesis |
| TRIM50 | tripartite motif containing 50 | 417461 | XM_415709 | Metabolism |
| DDI2 | DNA-damage inducible 1 homolog 2 (S. cerevisiae) | 425541 | XM_423293 | Metabolism |
| NPR2 | natriuretic peptide receptor B/guanylate cyclase B (atrionatriuretic peptide receptor B) | 100859339 | XM_003642919 | Metabolism |
| CNOT4 | CCR4-NOT transcription complex, subunit 4 | 417936 | NM_001012811 | Nucleic acid synthesis |
| CAPN13 | calpain 13 | 421304 | XM_419369 | Metabolism |
| DNASE1L2 | deoxyribonuclease I-like 2 | 427682 | XM_425256 | Metabolism |
| PHF21A | PHD finger protein 21A | 423199 | NM_001199647 | Nucleic acid synthesis |
| PCGF5 | polycomb group ring finger 5 | 423796 | XM_421668 | Nucleic acid synthesis |
| IFN alpha Receptor (IFNAR1) | interferon (alpha, beta and omega) receptor 1 | 395665 | NM_204859 | Immune response |
| IL-6 | interleukin 6 | 395337 | NM_204628 | Immune response |
| IL-1RA | interleukin 1 receptor, type I | 396481 | NM_205485 | Immune response |
| LAMP1 | lysosomal-associated membrane protein 1 | 396220 | NM_205283.2 | Immune response |
| EFR3A | EFR3 homolog A (S. cerevisiae) | 420327 | NC_006089.3 | Embryo development |
| ABI1 | abl-interactor 1 | 420489 | AJ720766.1 | Immune response |
| GADL1 | glutamate decarboxylase-like 1 | 100857134 | XM_003640735.2 | Metabolism |
| PLVAP | plasmalemma vesicle associated protein | 100857417 | XM_004950319.1 | Immune response |
| CYYR1 | cysteine/tyrosine-rich 1 | 770067 | XM_001233378.3 | Cell signalling |
| ASAP1 | ArfGAP with SH3 domain, ankyrin repeat and PH domain 1 | 428385 | XM_425945.4 | Immune response |
| NXF1 | nuclear RNA export factor 1 | 769691 | XM_001232980.3 | Nucleic acid synthesis |
| NSUN6 | NOP2/Sun domain family, member 6 | 428419 | XM_004939249.1 | Nucleic acid synthesis |
| ANGPTL7 | angiopoietin-like 7 | 101750033 | XM_004947467.1 | Embryo development |
| SIL1 | SIL1 nucleotide exchange factor | 416185 | XM_004944772.1 | Embryo development |
| BCAR3 | breast cancer anti-estrogen resistance 3 | 424494 | XM_004936593.1 | Immune response |
| GOLPH3L | Golgi phosphoprotein 3-like | 425072 | XM_004948290.1 | Nucleic acid synthesis |
| HN1 | hematological and neurological expressed 1 | 422119 | NM_001006425.1 | Embryo development |
| ADCY7 | adenylate cyclase 7 | 415732 | XM_414097.4 | Immune response |
| CBLN4 | cerebellin 4 precursor | 769254 | NM_001079487.1 | Metabolism |
| CXORF56 | chromosome 4 open reading frame, human CXorf56 | 428719 | XM_003641123.2 | |
| DDX10 | DEAD (Asp-Glu-Ala-Asp) box polypeptide 10 | 418965 | AJ720478.1 | Metabolism |
| EIF2S3 | Putative eukaryotic translation initiation factor 2 subunit 3-like protein | 418597 | NM_001006260.2 | Metabolism |
| ESF1 | nucleolar pre-rRNA processing protein homolog | 428551 | NM_001031519.1 | Nucleic acid synthesis |
| GCOM1 | GRINL1A complex locus 1 | 415404 | XM_413789.4 | Nucleic acid synthesis |
| GTPBP4 | GTP binding protein 4 | 420458 | NM_001006354.1 | Nucleic acid synthesis |

TABLE 1-continued

Antiviral genes and/or proteins

| Gene | Name | GENE ID | Ref SeqID mRNA | Pathway |
|---|---|---|---|---|
| KPNA3 | karyopherin alpha 3 | 418870 | CN232780.1 | Cell signalling |
| LRRIQ1 | Leucine-rich repeats and IQ motif containing 1 | 417882 | XM_416125.4 | Embryo development |
| LUC7L | LUC7-like (*S. cerevisiae*) | 416654 | XR_213192.1 | Nucleic acid synthesis |
| MRPL12 | mitochondrial ribosomal protein L12 | 769031 | XM_001232213.3 | Metabolism |
| POLR3E | polymerase (RNA) III (DNA directed) polypeptide E | 416620 | XM_414921.4 | Nucleic acid synthesis |
| PWP2 | PWP2 periodic tryptophan protein homolog (yeast) | 418551 | XM_416757.4 | Nucleic acid synthesis |
| RPL7A | ribosomal protein L7a | 417158 | NM_001004379.1 | Nucleic acid synthesis |
| SMYD2 | SET and MYND domain containing 2 | 421361 | NM_001277571.1 | Nucleic acid synthesis |
| XPO1 | exportin 1 (CRM1 homolog, yeast) | 421192 | NM_001290134.1 | Cell signalling |
| ZKSCAN7/ ZNF436 | zinc finger with KRAB and SCAN domains 7 | 416664 | XM_004945381.1 | |
| IFT43 | intraflagellar transport 43 homolog (*Chlamydomonas*) | 771922 | XM_004941812.1 | Embryo development |
| IFNα | IFNA3 interferon | 396398 | NM_205427.1 | Immune response |
| IFNβ | Interferon, beta | 554219 | NM_001024836.1 | Immune response |
| IFNλ (IFNL3) | interleukin 28B (interferon, lambda 3) | 770778 | NM_001128496.1 | Immune response |
| IFNγ | interferon gamma | 396054 | NM_205149.1 | Immune response |
| MDA5/IF1H1 | interferon induced with helicase C domain 1 | 424185 | NM_001193638.1 | Immune response |
| UBE1DC1/ UBA5 | ubiquitin-like modifier activating enzyme 5 | 414879 | NM_001001765.1 | Immune response |
| LOC100859339/ NPR2 | natriuretic peptide receptor B/guanylate cyclase B (atrionatriuretic peptide receptor B) | 100859339 | XM_003642919.2 | Immune response |
| IL28RA/ IFNLR1 | interferon, lambda receptor 1 | 419694 | XM_004947908.1 | Immune response |
| AHHR | aryl-hydrocarbon receptor repressor | 57491 | NM_020731.4 | Cell growth |
| ZNF334 | Zinc Finger Protein 334 | 55713 | NM_018102.4 | Immune response |
| SSR4 | Signal Sequence Receptor, Delta | 6748 | NM_001204526.1 | Protein translocation |
| KLRC1 | Killer Cell Lectin-Like Receptor Subfamily C, Member 1 | 3821 | NM_213658.2 | Immune response |
| SIX5 | SIX Homeobox 5 | 147912 | NM_175875.4 | Organogenesis |
| TCL1B | T-Cell Leukemia/ Lymphoma 1B | 9623 | NM_004918.3 | Immune response |
| ZNF211 | Zinc Finger Protein 211 | 10520 | NM_001265597.1 | Developmental processes |
| MAGEL2 | Melanoma Antigen Family L2 | 54551 | NM_019066.4 | Developmental processes |
| SBNO1 | Strawberry notch homolog 1 | 55206 | NM_001167856.1 | Developmental processes |
| OR1D5 | Olfactory Receptor, Family 1, Subfamily D, Member 5 | 8386 | NM_014566.1 | Olfactory receptor |
| SLC17A9 | Solute carrier family 17 (vesicular nucleotide transporter), member 9 | 63910 | NM_001302643.1 | Solute transport |
| ZNF607 | Zinc finger protein 607 | 84775 | NM_032689.4 | Gene expression |
| GCET2/ GCSAM | Germinal center B-cell expressed transcript 2 (GCET2) | 257144 | NM_001190259.1 | Cell signalling |
| TMEM223 | Transmembrane protein 223 | 79064 | NM_001080501.2 | |
| ZNF146 | Zinc finger protein 146 | 7705 | NM_007145.2 | Gene expression |
| NLRP13 | NLR family, pyrin domain containing 13 (NLRP13) | 126204 | NM_176810.2 | Inflammation |
| RLN2 | Relaxin 2 (RLN2) | 6019 | NM_134441.2 | Endocrine/autocrine hormone |

TABLE 1-continued

Antiviral genes and/or proteins

| Gene | Name | GENE ID | Ref SeqID mRNA | Pathway |
| --- | --- | --- | --- | --- |
| NCR2 | Natural cytotoxicity triggering receptor 2 | 9436 | NM_004828.3 | Immune response |
| OR4B1 | Olfactory receptor, family 4, subfamily B, member 1 | 119765 | NM_001005470.1 | Olfactory receptor |
| GLUD2 | Glutamate dehydrogenase 2 | 2747 | NM_012084.3 | Metabolism |
| HTRA4 | HtrA serine peptidase 4 | 203100 | NM_153692.3 | Protease |
| IFN alpha Receptor (IFNAR2) | interferon (alpha, beta and omega) receptor 2 | 395664 | NM_204858.1 | Immune response |
| IFNGR1 | Interferon Gamma Receptor 1 | 421685 | NM_001130387.1 | Immune response |
| IFNGR2 | Interferon Gamma Receptor 2 (Interferon Gamma Transducer 1) | 418502 | NM_001008676.2 | Immune response |
| IL10R2 | interleukin 10 receptor subunit beta | 395663 | NM_204857.1 | Immune response |
| IL1RB | Interleukin 1 receptor type 2 | 418715 | XM_416914.5 | Immune response |
| IFNκ/IFNK/IFN Kappa | interferon kappa | 56832 | NM_020124.2 | Immune response |
| IFNΩ/IFN omega | Interferon omega | 3467 | NM_002177.2 | Immune response |

Reducing Expression of an Antiviral Gene and/or Level of Antiviral Protein Activity in a Population of Cells Increased viral production can be achieved through the use of a genetically modified population of cells and/or a population of cells treated with an exogenous compounds as defined herein.

In some embodiments, the expression of the antiviral gene and/or protein in the population of cells is reduced by introduction of a genetic modification. In one example, the genetic modification is introduced directly into at least 10%, or at least 20%, or at least 30%, or at least 40%, or at least 50%, or at least 60%, or at least 70%, or at least 80%, or at least 85%, or at least 90%, or at least 95%, or 100% of cells of the population of cells. In an embodiment, the genetic modification is introduced into 100% of the population of cells. In an embodiment, the genetic modification is introduced into the ancestors of the population of cells. Introduction of the genetic modification results in the creation of a transgenic cell.

In some embodiments, the expression of the antiviral gene and/or protein activity in the population of cells is reduced by an exogenous compound. Examples of methods of exogenous compounds, include but are not limited to, a small carbon based molecule, a protein binding agent, a programmable nuclease, a polynucleotide or a combination of two or more thereof.

Genetic Modification

The genetic modification can be any man made change to a naturally occurring cell that achieves the desired effect, that being reduced expression of an antiviral gene and/or level of antiviral protein activity in the population of cells. Methods of genetically modifying cells are well known in the art. In an embodiment, the genetic modifications is a mutation of an endogenous gene which partially or completely inactivates the gene, such as a point mutation, an insertion, or a deletion (or a combination of one or more thereof). The point mutation may be a premature stop codon (a nonsense mutation), a splice-site mutation, a deletion, a frame-shift mutation or an amino acid substitution mutation that reduces activity of the gene or the encoded polypeptide.

In an embodiment, the genetic modification is introduced by a programmable nuclease. In an embodiment, the genetic modification is introduced by homologous recombination. In an embodiment, the genetic modification is introduced by non-homologous end joining. In an embodiment, the genetic modification is introduced by a chemical mutagen. In an alternative embodiment, the genetic modification is introduced by a transgene encoded by an exogenous polynucleotide. In an embodiment, the exogenous polynucleotide is encoded by a DNA molecule, a RNA molecule or a DNA/RNA hybrid molecule. Examples of exogenous polynucleotide which reduces expression of an endogenous gene are selected from the group consisting of an antisense polynucleotide, a sense polynucleotide, a microRNA, a polynucleotide which encodes a polypeptide which binds the endogenous enzyme, a transposon, an aptamer, a double stranded RNA molecule and a processed RNA molecule derived therefrom. In an embodiment, the transgene comprises an open reading frame encoding the polynucleotide operably linked to a promoter which directs expression of the polynucleotide in the population of cells.

Programmable Nucleases

In some embodiments, the genetic modification which reduces the expression of an antiviral gene in the population of cells when compared to isogenic cells lacking the genetic modification is introduced via a programmable nuclease. In some embodiments, the exogenous compound which reduces the expression of an antiviral gene and/or reduces the level of antiviral protein activity in the population of cells when compared to isogenic cells lacking the compound is a programmable nuclease.

As used herein, the term "programmable nuclease" relates to nucleases that are "targeted" ("programed") to recognize and edit a pre-determined site in a genome of a cell.

In an embodiment, the programmable nuclease can induce site specific DNA cleavage at a pre-determined site in a genome. In an embodiment, the programmable nuclease may be programmed to recognize a genomic location with a DNA binding protein domain, or combination of DNA binding protein domains. In an embodiment, the nuclease introduces a deletion, substitution or an insertion into the antiviral gene or a regulatory region thereof.

In an embodiment, the programmable nuclease may be programmed to recognize a genomic location by a combination of DNA-binding zinc-finger protein (ZFP) domains. ZFPs recognize a specific 3-bp in a DNA sequence, a combination of ZFPs can be used to recognize a specific a specific genomic location.

In an embodiment, the programmable nuclease may be programmed to recognize a genomic location by transcription activator-like effectors (TALEs) DNA binding domains.

In an alternate embodiment, the programmable nuclease may be programmed to recognize a genomic location by one or more RNA sequences. In an alternate embodiment, the programmable nuclease may be programmed by one or more DNA sequences. In an alternate embodiment, the programmable nuclease may be programmed by one or more hybrid DNA/RNA sequences. In an alternate embodiment, the programmable nuclease may be programmed by one or more of an RNA sequence, a DNA sequences and a hybrid DNA/RNA sequence.

In an alternate embodiment, the programmable nuclease can be used for multiplex silencing i.e. delivery of programmable nuclease with more than one "targeting" or "programming sequence" (i.e. two, three, four, five or more programming sequences) such that two, three, four, five or more antiviral genes to be targeted simultaneously (Kim et al., 2014).

Programmable nucleases that can be used in accordance with the present disclosure include, but are not limited to, RNA-guided engineered nuclease (RGEN) derived from the bacterial clustered regularly interspaced short palindromic repeat (CRISPR)-cas (CRISPR-associated) system, zinc-finger nuclease (ZFN), transcription activator-like nuclease (TALEN), and argonautes.

(CRISPR)-cas (CRISPR-associated) system is a microbial nuclease system involved in defence against invading phages and plasmids. CRISPR loci in microbial hosts contain a combination of CRISPR-associated (Cas) genes as well as non-coding RNA elements capable of programming the specificity of the CRISPR-mediated nucleic acid cleavage. Three types (I-III) of CRISPR systems have been identified across a wide range of bacterial hosts with II RGEN classes (Makarova et al., 2015). One key feature of each CRISPR locus is the presence of an array of repetitive sequences (direct repeats) interspaced by short stretches of non-repetitive sequences (spacers). The non-coding CRISPR array is transcribed and cleaved within direct repeats into short crRNAs containing individual spacer sequences, which direct Cas nucleases to the target site (protospacer).

The Type II CRISPR carries out targeted DNA double-strand break in four sequential steps (for example, see Cong et al., 2013). First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. The CRISPR system can also be used to generate single-stranded breaks in the genome. Thus, the CRISPR system can be used for RNA guided (or RNA programmed) site specific genome editing.

In an embodiment, the nuclease is a RNA-guided engineered nuclease (RGEN). In an embodiment, the RGEN is from an archaeal genome or is a recombinant version thereof. In an embodiment, the RGEN is from a bacterial genome or is a recombinant version thereof. In an embodiment, the RGEN is from a Type I (CRISPR)-cas (CRISPR-associated) system. In an embodiment, the RGEN is from a Type II (CRISPR)-cas (CRISPR-associated) system. In an embodiment, the RGEN is from a Type III (CRISPR)-cas (CRISPR-associated) system. In an embodiment, the nuclease is a class I RGEN. In an embodiment, the nuclease is a class II RGEN. In an embodiment, the RGEN is a multi-component enzyme. In an embodiment, the RGEN is a single component enzyme. In an embodiment, the RGEN is CAS3. In an embodiment, the RGEN is CAS10. In an embodiment, the RGEN is CAS9. In an embodiment, the RGEN is Cpf1 (Zetsche et al., 2015). In an embodiment, the RGEN is targeted by a single RNA or DNA. In an embodiment, the RGEN is targeted by more than one RNA and/or DNA. In an embodiment, the CAS9 is from *Steptococcus pyogenes*.

In an embodiment, the programmable nuclease may be a transcription activator-like effector (TALE) nuclease (see, e.g., Zhang et al., 2011). TALEs are transcription factors from the plant pathogen Xanthomonas that can be readily engineered to bind new DNA targets. TALEs or truncated versions thereof may be linked to the catalytic domain of endonucleases such as FokI to create targeting endonuclease called TALE nucleases or TALENs.

In an embodiment, the programmable nuclease is a zinc-finger nuclease (ZFN). In one embodiment, each monomer of the ZFN comprises 3 or more zinc finger-based DNA binding domains, wherein each zinc finger-based DNA binding domain binds to a 3 bp subsite. In other embodiments, the ZFN is a chimeric protein comprising a zinc finger-based DNA binding domain operably linked to an independent nuclease. In one embodiment, the independent endonuclease is a FokI endonuclease. In one embodiment, the nuclease agent comprises a first ZFN and a second ZFN, wherein each of the first ZFN and the second ZFN is operably linked to a FokI nuclease, wherein the first and the second ZFN recognize two contiguous target DNA sequences in each strand of the target DNA sequence separated by about 6 bp to about 40 bp cleavage site or about a 5 bp to about 6 bp cleavage site, and wherein the FokI nucleases dimerize and make a double strand break (see, for example, US20060246567, US20080182332, US20020081614, US20030021776, WO/2002/057308, US20130123484, US20100291048 and WO 11/017293).

In an embodiment, the programmable nuclease may be a DNA programmed argonaute (WO 14/189628). Prokaryotic and eukaryotic argonautes are enzymes involved in RNA interference pathways. An argonaute can bind and cleave a target nucleic acid by forming a complex with a designed nucleic acid-targeting acid. Cleavage can introduce double stranded breaks in the target nucleic acid which can be repaired by non-homologous end joining machinery. A DNA "guided" or "programmed" argonaute can be directed to introducing double stranded DNA breaks in predetermined locations in DNA. In an embodiment, the argonaute is from *Natronobacterium gregoryi*.

Homologous Recombination

In an embodiment, the genetic modification is introduced by homologous recombination. Homologous recombination is a type of genetic recombination in which nucleotide sequences are exchanged between two similar or identical molecules of DNA which can involve the use of the double-strand break repair (DSBR) pathway and the synthesis-dependent strands annealing (SDSA pathway) (Lodish et al., 2000; Weaver, 2002). Homologues recombination can be used to a delete a gene or portion thereof, or to introduce a substitution or an insertion into the antiviral gene or a regulatory region thereof. In addition, homologous recombination can be used to insert a transgene. Homologous recombination can be used to introduce a genetic modification into the DNA of a host cell by any method known to a person skilled in the art. In an embodiment, homologous recombination may be triggered by a programmable nuclease.

Double-Stranded RNA

In an embodiment, the exogenous polynucleotide is a dsRNA. In one embodiment, the genetic modification is a transgene which encodes a dsRNA molecule for RNAi, preferably integrated into the genome of a cell. In another embodiment, the exogenous compound is a dsRNA molecule for RNAi, or a transgene encoding the dsRNA (for instance provided in a suitable expression vector such as a virus).

The terms "RNA interference", "RNAi" or "gene silencing" refer generally to a process in which a dsRNA molecule reduces the expression of a nucleic acid sequence with which the double-stranded RNA molecule shares substantial or total homology. However, it has been shown that RNA interference can be achieved using non-RNA double stranded molecules (see, for example, US 20070004667).

The present invention includes nucleic acid molecules comprising and/or encoding double-stranded regions for RNA interference for use in the invention. The nucleic acid molecules are typically RNA but may comprise chemically-modified nucleotides and non-nucleotides.

The double-stranded regions should be at least 19 contiguous nucleotides, for example about 19 to 23 nucleotides, or may be longer, for example 30 or 50 nucleotides, or 100 nucleotides or more. The full-length sequence corresponding to the entire gene transcript may be used. Preferably, they are about 19 to about 23 nucleotides in length.

The degree of identity of a double-stranded region of a nucleic acid molecule to the targeted transcript should be at least 90% and more preferably 95-100%. The nucleic acid molecule may of course comprise unrelated sequences which may function to stabilize the molecule.

The term "short interfering RNA" or "siRNA" as used herein refers to a nucleic acid molecule which comprises ribonucleotides capable of inhibiting or down regulating gene expression, for example by mediating RNAi in a sequence-specific manner, wherein the double stranded portion is less than 50 nucleotides in length, preferably about 19 to about 23 nucleotides in length. For example the siRNA can be a nucleic acid molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The siRNA can be assembled from two separate oligonucleotides, where one strand is the sense strand and the other is the antisense strand, wherein the antisense and sense strands are self-complementary.

As used herein, the term siRNA is meant to be equivalent to other terms used to describe nucleic acid molecules that are capable of mediating sequence specific RNAi, for example micro-RNA (miRNA), short hairpin RNA (shRNA), short interfering oligonucleotide, short interfering nucleic acid (siNA), short interfering modified oligonucleotide, chemically-modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, siRNA molecules of the invention can be used to epigenetically silence genes at both the post-transcriptional level or the pre-transcriptional level. In a non-limiting example, epigenetic regulation of gene expression by siRNA molecules of the invention can result from siRNA mediated modification of chromatin structure to alter gene expression.

By "shRNA" or "short-hairpin RNA" is meant an RNA molecule where less than about 50 nucleotides, preferably about 19 to about 23 nucleotides, is base paired with a complementary sequence located on the same RNA molecule, and where said sequence and complementary sequence are separated by an unpaired region of at least about 4 to about 15 nucleotides which forms a single-stranded loop above the stem structure created by the two regions of base complementarity. An Example of a sequence of a single-stranded loop includes: 5' UUCAAGAGA 3'.

Included shRNAs are dual or bi-finger and multi-finger hairpin dsRNAs, in which the RNA molecule comprises two or more of such stem-loop structures separated by single-stranded spacer regions.

Once designed, the nucleic acid molecules comprising a double-stranded region can be generated by any method known in the art, for example, by in vitro transcription, recombinantly, or by synthetic means.

Modifications or analogues of nucleotides can be introduced to improve the properties of the nucleic acid molecules of the invention. Improved properties include increased nuclease resistance and/or increased ability to permeate cell membranes. Accordingly, the terms "nucleic acid molecule" and "double-stranded RNA molecule" includes synthetically modified bases such as, but not limited to, inosine, xanthine, hypoxanthine, 2-aminoadenine, 6-methyl-, 2-propyl- and other alkyl-adenines, 5-halo uracil, 5-halo cytosine, 6-aza cytosine and 6-aza thymine, pseudo uracil, 4-thiuracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine.

Small Molecules

In some embodiments, the exogenous compound is a small molecule. In an embodiment, the small molecule binds the antiviral protein thereby reducing the ability of the protein to perform its normal function in a virally infected cell.

In an embodiment, the compound that is administered may be a precursor compound which is inactive or comparatively poorly active, but which following administration is converted (e.g. metabolised) to a compound reduces the expression of an antiviral gene and/or protein activity in the population of cells when compared to isogenic cells lacking the compound. In those embodiments, the compound that is administered may be referred to as a prodrug. Alternatively or in addition, the compounds that are administered may be metabolized to produce active metabolites which have activity in reducing the expression of an antiviral gene and/or protein activity in the population of cells when compared to isogenic cells lacking the compound. The use of such active metabolites is also within the scope of the present disclosure.

Depending on the substituents present in the exogenous compound, the compound may optionally be present in the form of a salt. Salts of compounds which are suitable for use in in the invention are those in which a counter ion is pharmaceutically acceptable. Suitable salts include those formed with organic or inorganic acids or bases. In particular, suitable salts formed with acids include those formed with mineral acids, strong organic carboxylic acids, such as alkane carboxylic acids of 1 to 4 carbon atoms which are unsubstituted or substituted, for example, by halogen, such as saturated or unsaturated dicarboxylic acids, such as hydroxycarboxylic acids, such as amino acids, or with organic sulfonic acids, such as ($C_{1-4}$)-alkyl- or aryl-sulfonic acids which are substituted or unsubstituted, for example by halogen. Pharmaceutically acceptable acid addition salts include those formed from hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine. Pharmaceutically acceptable base salts include ammonium salts, alkali metal salts, for example those of potassium and sodium, alkaline earth metal salts, for example those of calcium and magnesium, and salts with organic bases, for example dicyclohexylamine, N-methyl-D-glucomine, morpholine, thiomorpholine, piperidien, pyrrolidine, a mono-, di- or tri-lower alkylamine, for example ethyl-, t-butyl-, diethyl-, diisopropyl-, triethyl-, tributyl- or dimethyl-propylamine, or a mono-, di- or trihydroxy lower alkylamine, for example mono-, di- or triethanolamine. Corresponding internal salts may also be formed.

Those skilled in the art of organic and/or medicinal chemistry will appreciate that many organic compounds can form complexes with solvents in which they are reacted or from which they are precipitated or crystallised. These complexes are known as "solvates". For example, a complex with water is known as a "hydrate". Solvates, such as hydrates, exist when the drug substance incorporates solvent, such as water, in the crystal lattice in either stoichiometric or non-stoichiometric amounts. Drug substances are routinely screened for the existence of solvates such as hydrates since these may be encountered at any stage. Accordingly it will be understood that the compounds useful for the present invention may be present in the form of solvates, such as hydrates. Solvated forms of the compounds which are suitable for use in the invention are those wherein the associated solvent is pharmaceutically acceptable. For example, a hydrate is an example of a pharmaceutically acceptable solvate.

The compounds useful for the present invention may be present in amorphous form or crystalline form. Many compounds exist in multiple polymorphic forms, and the use of the compounds in all such forms is encompassed by the present disclosure.

Small molecules useful for the present disclosure can be identified using standard procedures such as screening a library of candidate compounds for binding to an antiviral target protein of the invention, and then determining if any of the compounds which bind reduce protein activity. For example, a small molecule useful for reducing activity of the chicken IFN-α/β receptor 1 would bind the receptor and inhibit the ability of a ligand of the receptor (such as IFNα) to induce a cellular signal.

Binding Agents

In an embodiment, the exogenous compound is a protein which binds and reduces the activity of the antiviral protein. In an embodiment, the binding agent is an antibody or a fragment thereof. In some embodiments, the antibody is directed at and/or reduces the expression or activity of DDI2, HSBP1, GNAZ, NPR2, CNOT4, MDA5, IFNα, IL-6, IFNAR1, IFNβ, IFNγ, IFNλ, UBE1DC1, CDX2, LOC100859339, IL28RA, ZFPM2, TRIM50, DNASEIL2, PHF21A, GAPDH, BACE2, PCGF5, IL-1RA, CAPN13, UBA5, IFIH1, LAMP1, EFR3A, ARRDC3, ABI1, SCAF4, GADL1, ZKSCAN7, PLVAP, RPUSD1, CYYR1, UPF3A, ASAP1, NXF1, TOP1MT, RALGAPB, SUCLA2, GORASP2, NSUN6, CELF1, ANGPTL7, SLC26A6, WBSCR27, SIL1, HTT, MYOC, TM9SF2,CEP250, FAM188A, BCAR3, GOLPH3L, HN1, ADCY7, AKAP10, ALX1, CBLN4, CRK, CXORF56, DDX10, EIF2S3, ESF1, GBF1, GCOM1, GTPBP4, HOXB9, IFT43, IMP4, ISY1, KIAA0586, KPNA3, LRRIQ1, LUC7L, MECR, MRPL12, POLR3E, PWP2, RPL7A, SERPINH1, SLC47A2, SMYD2, STAB1, TTK, WNT3, XPO1, AHHR, ZNF334, SSR4, KLRC1, SIX5, TCL1B, ZNF211, MAGEL2, SBN01, OR1D5, SLC17A9, ZNF607, GCET2, TMEM223, ZNF146, NLRP13, RLN2, NCR2, OR4B1, GLUD2, IFNAR2, IFNGR1, INFGR2, IL-10R2, IFNκ, IFNΩ, IL-1RB and HTRA4. gene and/or protein or the corresponding receptor or agonist thereof. In some embodiments the binding agent is a bispecific antibody directed at any combination of two or more of: DDI2, HSBP1, GNAZ, NPR2, CNOT4, MDA5, IFNα, IL-6, IFNAR1, IFNβ, IFNγ, IFNλ, UBE1DC1, CDX2, LOC100859339, IL28RA, ZFPM2, TRIM50, DNASEIL2, PHF21A, GAPDH, BACE2, PCGF5, IL-1RA, CAPN13, UBA5, IFIH1, LAMP1, EFR3A, ARRDC3, ABI1, SCAF4, GADL1, ZKSCAN7, PLVAP, RPUSD1, CYYR1, UPF3A, ASAP1, NXF1, TOP1MT, RALGAPB, SUCLA2, GORASP2, NSUN6, CELF1, ANGPTL7, SLC26A6, WBSCR27, SIL1, HTT, MYOC, TM9SF2,CEP250, FAM188A, BCAR3, GOLPH3L, HN1, ADCY7, AKAP10, ALX1, CBLN4, CRK, CXORF56, DDX10, EIF2S3, ESF1, GBF1, GCOM1, GTPBP4, HOXB9, IFT43, IMP4, ISY1, KIAA0586, KPNA3, LRRIQ1, LUC7L, MECR, MRPL12, POLR3E, PWP2, RPL7A, SERPINH1, SLC47A2, SMYD2, STAB1, TTK, WNT3, XPO1, AHHR, ZNF334, SSR4, KLRC1, SIX5, TCL1B, ZNF211, MAGEL2, SBN01, OR1D5, SLC17A9, ZNF607, GCET2, TMEM223, ZNF146, NLRP13, RLN2, NCR2, OR4B1, GLUD2, IFNAR2, IFNGR1, INFGR2, IL-10R2, IFNκ, IFNΩ, IL-1RB and HTRA4 or a receptor or agonist thereof. In an embodiment, the antibody is an antibody modified to penetrate or be taken up (passively or actively) by a cell. In an embodiment, the binding agent is not B18R.

The term “antibody” as used herein includes polyclonal antibodies, monoclonal antibodies, bispecific antibodies, fusion diabodies, triabodies, heteroconjugate antibodies, chimeric antibodies including intact molecules as well as fragments thereof, and other antibody-like molecules. Antibodies include modifications in a variety of forms including, for example, but not limited to, domain antibodies including either the VH or VL domain, a dimer of the heavy chain variable region (VHH, as described for a camelid), a dimer of the light chain variable region (VLL), Fv fragments containing only the light (VL) and heavy chain (VH) variable regions which may be joined directly or through a linker, or Fd fragments containing the heavy chain variable region and the CH1 domain.

A scFv consisting of the variable regions of the heavy and light chains linked together to form a single-chain antibody (Bird et al., 1988; Huston et al., 1988) and oligomers of scFvs such as diabodies and triabodies are also encompassed by the term "antibody". Also encompassed are fragments of antibodies such as Fab, (Fab')2 and FabFc2 fragments which contain the variable regions and parts of the constant regions. Complementarity determining region (CDR)-grafted antibody fragments and oligomers of antibody fragments are also encompassed. The heavy and light chain components of an Fv may be derived from the same antibody or different antibodies thereby producing a chimeric Fv region. The antibody may be of animal (for example mouse, rabbit or rat) or may be chimeric (Morrison et al., 1984). The antibody may be produced by any method known in the art.

Using the guidelines provided herein and those methods well known to those skilled in the art which are described in the references cited above and in such publications as Harlow & Lane, Antibodies: a Laboratory Manual, Cold Spring Harbor Laboratory, (1988) the antibodies for use in the methods of the present invention can be readily made.

The antibodies may be Fv regions comprising a variable light (VL) and a variable heavy (VH) chain in which the light and heavy chains may be joined directly or through a linker. As used herein a linker refers to a molecule that is covalently linked to the light and heavy chain and provides enough spacing and flexibility between the two chains such that they are able to achieve a conformation in which they are capable of specifically binding the epitope to which they are directed. Protein linkers are particularly preferred as they may be expressed as an intrinsic component of the Ig portion of the fusion polypeptide.

In one embodiment, the antibodies have the capacity for intracellular transmission. Antibodies which have the capacity for intracellular transmission include antibodies such as camelids and llama antibodies, shark antibodies (IgNARs), scFv antibodies, intrabodies or nanobodies, for example, scFv intrabodies and VHH intrabodies. Such antigen binding agents can be made as described by Harmsen and De Haard (2007), Tibary et al. (2007) and Muyldermans et al. (2001). Yeast SPLINT antibody libraries are available for testing for intrabodies which are able to disrupt protein-protein interactions (see for example, Visintin et al. (2008) for methods for their production). Such agents may comprise a cell-penetrating peptide sequence or nuclear-localizing peptide sequence such as those disclosed in Constantini et al. (2008). Also useful for in vivo delivery are Vectocell or Diato peptide vectors such as those disclosed in De Coupade et al. (2005) and Meyer-Losic et al. (2006).

In addition, the antibodies may be fused to a cell penetrating agent, for example a cell-penetrating peptide. Cell penetrating peptides include Tat peptides, Penetratin, short amphipathic peptides such as those from the Pep-and MPG-families, oligoarginine and oligolysine. In one example, the cell penetrating peptide is also conjugated to a lipid (C6-C18 fatty acid) domain to improve intracellular delivery (Koppelhus et al., 2008). Examples of cell penetrating peptides can be found in Howl et al. (2007) and Deshayes et al. (2008). Thus, the invention also provides the use of antibodies fused via a covalent bond (e.g. a peptide bond), at optionally the N-terminus or the C-terminus, to a cell-penetrating peptide sequence.

Nucleic Acid Constructs

Introduction of a genetic modification into the population of cells of the present invention may involve the use of nucleic acid construct. In an embodiment, the nucleic acid construct may comprise a transgene. As used herein, "nucleic acid construct" refers to any nucleic acid molecule that encodes, for example, a double-stranded RNA molecule as defined herein, a RNA, DNA or RNA/DNA hybrid sequences which "guides" or "targets" a programmable nuclease, or a polynucleotide of interest in a vector. Typically, the nucleic acid construct will be double stranded DNA or double-stranded RNA, or a combination thereof. Furthermore, the nucleic acid construct will typically comprise a suitable promoter operably linked to an open reading frame encoding the polynucleotide. The nucleic acid construct may comprise, for example, a first open reading frame encoding a first single strand of the double-stranded RNA molecule, with the complementary (second) strand being encoded by a second open reading frame by a different, or preferably the same, nucleic acid construct. The nucleic acid construct may be a linear fragment or a circular molecule and it may or may not be capable of replication. The skilled person will understand that the nucleic acid construct of the invention may be included within a suitable vector. Transfection or transformation of the nucleic acid construct into a recipient cell allows the cell to express an RNA or DNA molecule encoded by the nucleic acid construct.

In another example, the nucleic acid construct may express multiple copies of the same, and/or one or more (e.g. 1, 2, 3, 4, 5, or more) including multiple different, RNA molecules comprising a double-stranded region, for example a short hairpin RNA. In one example, the nucleic acid construct, is a construct suitable for homologous recombination.

The nucleic acid construct also may contain additional genetic elements. The types of elements that may be included in the construct are not limited in any way and may be chosen by one with skill in the art. In some embodiments, the nucleic acid construct is inserted into a host cell as a transgene. In such instances it may be desirable to include "stuffer" fragments in the construct which are designed to protect the sequences encoding the RNA molecule from the transgene insertion process and to reduce the risk of external transcription read through. Stuffer fragments may also be included in the construct to increase the distance between, e.g., a promoter and a coding sequence and/or terminator component. The stuffer fragment can be any length from 5-5000 or more nucleotides. There can be one or more stuffer fragments between promoters. In the case of multiple stuffer fragments, they can be the same or different lengths. The stuffer DNA fragments are preferably different sequences. Preferably, the stuffer sequences comprise a sequence identical to that found within a cell, or progeny thereof, in which they have been inserted. In a further embodiment, the nucleic acid construct comprises stuffer regions flanking the open reading frame(s) encoding the double stranded RNA(s).

Alternatively, the nucleic acid construct may include a transposable element, for example a transposon characterized by terminal inverted repeat sequences flanking the open reading frames encoding the double stranded RNA(s). Examples of suitable transposons include Tol2, mini-Tol, Sleeping Beauty, Mariner and Galluhop.

Other examples of an additional genetic element which may be included in the nucleic acid construct include a reporter gene, such as one or more genes for a fluorescent marker protein such as GFP or RFP; an easily assayed enzyme such as beta-galactosidase, luciferase, beta-glucuronidase, chloramphenical acetyl transferase or secreted embryonic alkaline phosphatase; or proteins for which immunoassays are readily available such as hormones or cytokines. Other genetic elements that may find use in embodiments of the present invention include those coding for proteins which confer a selective growth advantage on cells such as adenosine deaminase, aminoglycodic phosphotransferase, dihydrofolate reductase, hygromycin-B-phosphotransferase, or drug resistance.

Where the nucleic acid construct is to be transfected into a cell, it is desirable that the promoter and any additional genetic elements consist of nucleotide sequences that naturally occur in the hosts genome.

In some instances it may be desirable to insert the nucleic acid construct into a vector. The vector may be, e.g., a plasmid, virus or artificial chromosome derived from, for example, a bacteriophage, adenovirus, adeno-associated virus, retrovirus, poxvirus or herpesvirus. Such vectors include chromosomal, episomal and virus-derived vectors, e.g., vectors derived from bacterial plasmids, bacteriophages, and viruses, vectors derived from combinations thereof, such as those derived from plasmid and bacteriophage genetic elements, cosmids and phagemids.

In an embodiment, the nucleic acid construct comprises a promoter. The skilled person will appreciate that a promoter such as a constitutive promoter or an inducible promoter can be used in the present invention. In an embodiment, the promoter is a Pol I, Pol II or Pol II promoter. In an embodiment, the promoter is an avian promoter. Examples of avian promoters include the 7sK RNA polymerase III Promoter, U6 RNA polymerase II promoter (Bannister et al., 2007; Massine et al., 2005).

Viruses

Viruses which can be produced in the population of cells of the invention include any virus capable of replicating and producing new viral particles in a population of cells cultured under cull culture conditions. Such viruses include DNA and RNA viruses. In an embodiment, the virus is an animal virus. In an embodiment, the animal virus is a human virus. In an embodiment, the virus is a non-human virus. In an embodiment, the virus is an avian virus.

Examples of viruses for use in the present invention include, but are not limited to, viruses in a family selected from: Orthomyxoviridae, Herpesviridae, Paramyxoviridae, Flaviviridae and Coronaviridae.

The Orthomyxoviridae virus may be, for example, Influenza A virus, Influenza B virus, Influenza C virus, Isavirus, Thogotovirus and/or Quaranjavirus. The influenza virus may be an Influenza A virus. The Influenza A virus may be selected from Influenza A viruses isolated from an animal. In an embodiment, the animal is a human or an avian. In particular, the Influenza A virus may be selected from H1N1, H1N2, H1N3, H1N4, H1N5, H1N6, H1N7, H1N9, H2N1, H2N2, H2N3, H2N4, H2N5, H2N7, H2N8, H2N9, H3N1, H3N2, H3N3, H3N4, H3N5, H3N6, H3N8, H4N1, H4N2, H4N3, H4N4, H4N5, H4N6, H4N8, H4N9, H5N1, H5N2, H5N3, H5N6, H5N7, H5N8, H5N9, H6N1, H6N2, H6N3, H6N4, H6N5, H6N6, H6N7, H6N8, H6N9, H7N1, H7N2, H7N3, H7N4, H7N5, H7N7, H7N8, H7N9, H9N1, H9N2, H9N3, H9N5, H9N6, H9N7, H9N8, H10N1, H10N3, H10N4, H10N6, H10N7, H10N8, H10N9, H11N2, H11N3, H11N6, H11N9, H12N1, H12N4, H12N5, H12N9, H13N2, H13N6, H13N8, H13N9, H14N5, H15N2, H15N8, H15N9 and H16N3. In one embodiment, the Influenza A virus is selected from H1N1, H3N2, H7N7, and/or H5N1.

The Herpesviridae virus may be, for example, a HSV-1, HSV-2, varicella zoster virus, Epstein-barr virus or Cytomegalovirus.

The Paramyxoviridae virus may be, for example, a Paramyxovirinae or Pneumovirinae. In an embodiment, the Paramyxoviridae virus is Newcastle disease virus.

The Flaviviridae may be, for example, a Flavivirus, Hepacivirus, Pegivirus, Pestivirus. In an embodiment, the Flaviviridae may be the Apoi virus, Aroa virus, Bagaza virus, Banzi virus, Bouboui virus, Bukalasa bat virus, Cacipacore virus, Carey Island virus, Cowbone Ridge virus, Dakar bat virus, Dengue virus, Edge Hill virus, Entebbe bat virus, Gadgets Gully virus, Ilheus virus, Israel turkey meningoencephalomyelitis virus, Japanese encephalitis virus, Jugra virus, Jutiapa virus, Kadam virus, Kedougou virus, Kokobera virus, Koutango virus, Kyasanur Forest disease virus, Langat virus, Louping ill virus, Meaban virus, Modoc virus, Montana myotis leukoencephalitis virus, Murray Valley encephalitis virus, Ntaya virus, Omsk hemorrhagic fever virus, Phnom Penh bat virus, Powassan virus, Rio Bravo virus, Royal Farm virus, Saboya virus, Sal Vieja virus, San Perlita virus, Saumarez Reef virus, Sepik virus, St. Louis encephalitis virus, Tembusu virus, Tick-borne encephalitis virus, Tyuleniy virus, Uganda S virus, Usutu virus, Wesselsbron virus, West Nile virus, Yaounde virus, Yellow fever virus, Yokose virus, Zika virus The Coronaviradae virus may be, for example, a Coronavirinae or a Corovirinae. The Coronavirinae may be a Alphacoronavirus, Betacoronavirus, Deltacoronavirus, or Gammacoronavirus. The Torovirinae may be a Alphacoronavirus or Betacoronavirus. In on embodiment, the Coronaviradae may be the SARS (severe acute respiratory syndrome) coronavirus.

In an embodiment, the virus in selected from: Influenza virus, Canine distemper virus, Measles virus, Reovirus, Eastern equine encephalitis virus, Canine parainfluenza virus, Rabies virus, Fowlpox virus, Western equine encephalitis virus, Mumps virus, Equine encephalomyelitis, Rubella virus, Egg drop syndrome virus, Avian oncolytic viruses, Avian infectious laryngotracheitis Herpesvirus, Newcastle disease virus, Bovine parainfluenza virus, Smallpox virus, Infectious bursal disease, Bovine Ibaraki virus, Recombinant poxvirus, Avian adenovirus type I, II or III, Swine Japanese encephalitis virus, Yellow fever virus, Herpes virus, Sindbis virus, Infections bronchitis virus, Semliki forest virus, Encephalomyelitis virus, Venezuelan EEV virus, Chicken anaemia virus, Marek's disease virus, Parvovirus, Foot and mouth disease virus, Porcine reproductive and respiratory syndrome virus, Classical swine fever virus, Bluetongue virus, Kabane virus, Infectious salmon anaemia virus, Infectious hematopoietic necrosis virus, Viral haemorrhagic septicemia virus and Infectious pancreatic necrosis virus.

Cells and Cell Culture

The skilled person would understand that the cells of invention can be any cells which can be cultured in vitro and in which a virus can replicate. In one example, the cells are of mammalian, avian or Arthropoda origin. In one example, the cells are mammalian. In one example, the cells are avian. In one example, the avian cells are chicken cells. In one example, the cells are from a continuous cell line (Josefsberg et al., 2012). In one example, the cells are from a primary cell line. In one example, the cells are from an immortalized cell line. In one example, the cells are adherent cells. In one example, the cells are non-adherent cells (suspension cells). In one example, the cells are from a primary cell line derived from a chicken tissue. In one example, the cells are from a primary cell line from an egg. In one embodiment, the egg is an avian egg.

In one example, the cells are from a primary cell line derived from chicken embryonic fibroblasts (CEF). In one example, the cells are from avian embryonic-derived stem cell line EB14 (chicken) or EB66 (duck) (WO2005042728). In one example, the cells are from an immortalized cell line from a chicken. In one example, the cells are from the immortalized chick embryo cell line PBS-1 (Smith et al., 2008). In one example, the cells are from the chicken fibroblast cell line DF-1 (Himly et al., 1998). In one example, the cells are Madin-Darby canine kidney (MDCK) cells. In one example, the cells are MDCK 33016 cells. In one example, the cells are MDCK CCL34 cells. In one example, the cells African green monkey kidney-derived Vero cells. In one example, the cells are human retina derived PER.C6 cells. In one example, the cells are AGE1.CR cells. In one example, the cells are derived from the MRC-5 diploid cell line. In one example, the cells are human embryo kidney cells (HEK293). In one example, the cells are HeLa cells. In one example, the cells are insect cells. In one example, the insect cells are derived from *Trichoplusia*. In one example, the cells can be cultured in the absence of serum. In one example, the cells are cultured in the presence of serum.

The population of cells of the present invention can be cultured in any cell culture medium that allows the expansion of the cells in vitro and preferably, allows for infection of the cells by a virus. Such mediums and processes will be known to the skilled person (see, for example, Genzel et al., 2009; Josefsberg et al., 2012; Wolf et al., 2011). Exemplary cell culture mediums for culturing the population of cells of the present invention include, but are not limited to: Iscove's medium, UltraCHO, CD Hybridoma serum free medium, episerf medium, MediV SF103 (serum free medium), Dulbecco's modified eagle medium (DMEM), Eagles Modified Eagle Medium (EMEM), Glasgow's modified eagle medium (GMEM), SMIP-8, modified eagle medium (MEM), VP-SFM, DMEM based SFM, DMEM/F12, DMEM/Ham's F12, VPSFM/William's medium E, ExCell 525(SFM), adenovirus expression medium (AEM) and Excell 65629 (Genzel et al., 2009). It will be appreciated by persons skilled in the art that such mediums may be supplemented with additional growth factors, for example, but not limited, amino acids, hormones, vitamins and minerals. Optionally, such mediums may be supplemented with serum, for example fetal calf serum.

In one example, the cells are cultured using the batch cell culture process. In one example, the cells are cultured using the perfusion cell culture process. In one example, the cells are cultured in a seed medium and a production medium. In one example, the cells are cultured in a stirred-tank reactor. In one example, the volume of the reactor is from about 1 L to about 2500 L. In one example, the cells are cultured in a wave bioreactor. In one example, the cells are cultured in a cell factory system e.g. a Nunc cell factory system (Genzel et al., 2009).

In one example, a virus is added to the cell culture medium to infect the cells with a virus. In a further example, to infect the cells with the virus, the cell culture medium may be removed and replaced with a medium comprising the virus. For viral infection of adherent cells a protease may be added to the cell culture medium or the cell culture medium replaced with a medium comprising a protease to allow/enhance infection of the cells with the virus. In one example, the protease is trypsin or chymotrypsin.

In one example, the cells are cultured in the presence of the virus for a predetermined period of time to replicate the virus before harvesting of the replicated virus or particles thereof. In one example, the predetermined period of time is at least 8 hours, or at least 12 hours, or at least 18 hours, or at least 24 hours, or at least 48 hours, or at least three days, or at least 4 days, or at least 5 days, or at least 6 days, or at least 7 days, or at least 8 days, or at least 9 days, or at least 10 days, or at least 11 days, or at least 12 days, or at least 13 days, or at least 14 days, or at least 15 days. Virus grown as described herein can be used to produce, for example, live attenuated whole virus, inactivated whole virus, split virus particles or subunit virus particles suitable for use in vaccine compositions.

Harvesting Replicated Virus or Particles Thereof

The replicated virus or particles thereof (such as split virus particles or subunit virus particles) can be harvested from the population of cells, the secretions of cells (the cell culture medium also referred to as the supernatant) or a combination thereof by any method known to the skilled person. For example, harvesting of replicated virus or particles thereof can involve one or more of the following steps: clarification, concentration, inactivation, nuclease treatment, separation/purification, polishing and sterile filtration (Wolf et al., 2008; Wolf et al., 2011; Kalbfuss et al., 2006; Milian et al., 2015; Grein et al., 2013; Josefsberg et al., 2012). In one example, clarification is performed by centrifugation, microfiltration and/or depth filtration. In one example, concentration is performed by centrifugation, ultrafiltration, precipitation, monoliths and/or membrane adsorber. In one example, inactivation is performed by UV, heat or chemical treatment. Chemical forms of inactivation include formalin, binary ethyleneimine and β-propiolactone or any other method known to the skilled person. In an embodiment, the nuclease treatment is treatment with benzonase. In one example, separation/purification is performed by ultracentrifugation (for example density gradient), bead chromatography (for example size exclusion chromatography, ion exchange chromatography or affinity chromatography), and/or membrane adsorber (for example ion exchange chromatography or affinity chromatography). In one example, polishing is performed by ultrafiltration and/or diafiltration. In one example, virus or virus particles can be concentrated by alcohol or polyethylene glycol precipitation. In one example, harvesting the replicated virus or particles thereof comprises the use of a membrane as described in Grein et al. (2013).

In another example, the harvesting the replicated virus may include a virus disruption step to produce virus particles of a suitable size for a split vaccine composition or a subunit vaccine composition (Wolf et al., 2008; Josefsberg et al., 2012). Such a step can be any method that produces virus particles of a suitable size for a split vaccine composition or a subunit vaccine composition. In one example, the disruption step is detergent solubilisation.

In another example, harvesting of the replicated virus or particles thereof can involve one or more of the following steps: clarification, concentration separation, inactivation, nuclease treatment and/or polishing (Wolf et al., 2008). In one example, clarification is performed by diafiltration. In one example, concentration/separation is performed by affinity membrane adsorber. In one example, inactivation is performed by chemical treatment. Chemical forms of inactivation include formalin, binary ethyleneimine and β-propiolactone. In an embodiment, the nuclease treatment is treatment with benzonase. In an embodiment, polishing is performed by ultrafiltration and/or diafiltration.

In another example, harvesting the replicated virus or particles thereof can involve the steps used in preparation of the influenza vaccine influvac comprising performing the following steps on the supernatant from cell culture: capturing the virus particles using ion exchange chromatography, prefiltration, concentration/buffer exchange by ultra and diafiltration, nuclease treatment and virus inactivation with formaldehyde treatment (Wolf et al., 2008).

In another example, harvesting the replicated virus or particles thereof can involve the steps used in the preparation of cell culture-derived (such as Vero cell culture-derived) influenza vaccines comprising: clarification by low speed centrifugation, concentration by ultrafiltration, purification on a sucrose gradient, inactivation by formalin treatment, nuclease treatment with benzonase and diafiltration to remove the formalin (Wolf et al., 2008).

The skilled person would understand that harvested virus (whole attenuated or inactivated) or harvested virus particles (such as split virus particles or subunit virus particles) can be formulated into vaccine compositions. Such compositions can comprise one or more of: an adjuvant, an excipient, a binder, a preservative, a carrier coupling, a buffering agent, a stabilizing agent, an emulsifying agents, a wetting agent, a non-viral vector and a transfection facilitating compound (Josefsberg et al., 2011; Jones, 2008). The skilled person would further understand that such vaccine compositions can be lyophilized. In one example, the vaccine composition produced is suitable for human use. In one example, the vaccine composition produced is suitable for veterinary use.

EXAMPLES

Example 1

Disruption of Interferon Response by Neutralizing Antibodies Increases Viral Yield In Ovo The ORF of ChIFNα, ChIFNβ, ChIFNγ and ChIFNλ were expressed in Top F'10 *Escherichia coli* (*E. coli*) competent cells using a pQE50 expression system and after induction with IPTG. Recombinant protein was solubilised and purified using Ni-NTA-Agarose. Biological activities of rchIFNs were measured using a virus neutralization assay (Lowenthal et al., 1995). rchIFNs protected cells over a range of concentrations and therefore are biologically active (FIG. 1).

The rchIFNs were used as immunogens to generate rabbit antiserum against the homologous recombinant protein. New Zealand female white rabbits were immunized subcutaneously with the rchIFN protein in *Quilaja saponaria* (Quil A) cocktail adjuvant up to 7 times. Ammonium sulphate was used to enrich the globular serum proteins in the rabbit anti-chIFN antiserum. Enriched antisera were quantified using a Spectrophotometer (NanoDrop® ND-1000, NanoDrop Technologies, USA) prior to 0.2 μm filter sterilization (Sartorius, Germany) of the antibodies for in ovo injection. Reactivity of the sera and polyclonal antibody recognition was tested using and Indirect ELISA analysis. In brief, purified rchIFNs were diluted to 5 μg/mL in coating buffer in 96-well ELISA plates read at 450 nm on a Titertek Multiscan Plus plate reader. The analysis showed a dose-effect reactivity of the serum against the corresponding protein (FIG. 2A).

Next, Hyline brown eggs (Hy-Line, Australia) at embryonic age day 10-11 were inoculated via allantoic fluid with antibody and/or virus. Stocks of influenza virus (provided by CSL Pty Ltd) were diluted to 10-5 in virus diluent containing 1% neomycin/polymyxin. PR8 (H1N1) or H5N1 vaccine virus (NIBRG-14) (CSL, Australia) inoculations of eggs were performed separately. Purified anti-chIFN and anti-chIL-6 antibodies were also diluted in virus diluent solution for inoculation into eggs at either 1000 μg, 200 μg or 20 μg per egg. After inoculation eggs were incubated at 35° C. for 48 h.

The eggs were candled after incubation to check viability prior to being chilled O/N at 4° C. in preparation for harvesting. Allantoic fluid (5 mL) was removed from each egg for further analysis. HA assays were performed on the same day as harvest. Briefly, allantoic fluid samples were serial diluted ½5 in PBS and added in duplicate to the last row of round bottomed 96 well plates (ICN Biochemicals, USA). 50 μL of 0.5% of washed chicken RBC was added to all wells, gently tapped to mix and left at RT for at least 40 min and HA end point was determined. Experiments in ovo indicated that the anti-chIFN-α antibodies (FIG. 2B) and anti-chIFN-β antibodies (FIG. 2C) at all concentrations did not have a significant effect on the HA titre of either PR8 or NIBRG-14 virus in the eggs. However, the anti-chIFN4, antibodies (FIG. 3A) were shown to statistically improve the titre of PR8 virus when administered at 200 μg/egg ($p=0.04$). The H5N1 vaccine virus titre was statistically improved, up to 1.5 fold, when the antibodies were injected at both 1000 μg/egg ($p=0.0045$) and at 20 μg/egg ($p=0.0001$). Similarly, anti-chIFN-γ antibodies (FIG. 3B), when inoculated at 1000 μg/egg ($p=0.015$), were capable of improving the HA titre of the H5N1 vaccine virus. Furthermore, the anti-chIL-6 antibodies (FIG. 3C) also statistically enhanced H5N1 vaccine virus titres in eggs.

Example 2

Disruption of Numerous Genes by siRNA In Vitro Increases Viral Titres In Vitro

In order to identify gene candidates with an antiviral function a set of genes were evaluated by small interference RNA (siRNA) assay. DF-1 cells were transfected with a multiplex (smartpool) of siRNA against each gene prior infection with avian influenza (AI) virus. The results show an increase in viral titres after KD without any apparent toxic effect on the cells (FIG. 4). At least in some instances no apparent affect was observed but this may be due to the siRNA not being administered early enough to produce efficient KD (for example, considering the anti-IL6 antibody data this will most likely explain the IL-6 siRNA data in FIG. 4). For CNOT4, IFNAR or MDA5 the effect of individual smartpool siRNAs on cell viability and gene silencing was assessed (FIG. 5).

Example 3

Down-Regulation of Numerous Genes by shRNA In Ovo Increases Viral Titres

For in ovo analysis, siRNA was delivered as complexes with ABA-21/117Q/PF polymer (ABA-21/117Q; polymer without PolyFluor 570 dye labels) at molar ratios of 4:1 of polymer to 2 nmol siRNA in a total of 200 μl. Complexes were formed in aqueous solution in the presence of phosphate-buffered saline (PBS). The required amount of polymer (316 μg), resuspended in water, was added to the tubes and mixed by vortexing. A total of 2 nmol, equivalent to 30 μg of siControl or 24.5 μg of siAntiIFNAR1 was then added to the tubes and the sample vortexed. Complexion was allowed to continue for 1 h at room temperature. Complexes were injected directly into the corioallantoic fluid. After 48 hours virus was injected as previously described and samples were collected 24 hours after virus infection. Results show an increase of virus growth after KD of IFNAR1 (FIG. 6 and FIG. 7).

Example 4

Deletion of the IFNAR1 Gene in Chickens Increases Viral Titres In Vitro

To probe that permanent deletion of the chicken interferon (alpha, beta and omega) receptor 1, IFNAR1 (Gene ID: 395665) have an effect on viral yield; KO cell lines from the continuous cell line of chicken embryo fibroblasts (DF-1) were generated. Using the RNA-guided Cas9 nuclease from the microbial clustered regularly interspaced short palindromic repeats (CRISPR/Cas9) system, two different single guides RNA (sgRNA) were designed in order to produce a dual double-strand break by duplexing. sgRNA were cloned according to (Ran et al., 2013) and the corresponding constructs were transfected into DF-1 cells using encoding the deletion of around 200 bp removed entirely the transcription start site (TSS) and exon one of the IFNAR1 precursor. Single cells were isolated after sorting using a BD FACS Aria II™ cell sorter. The deletion in each clone was identified after genomic PCR screening to distinguish between wild type and monoallelic and biallelic targeted cell lines.

After transfection around 30% of the alleles presented a deletion of more than 200 bp that was confirmed by cloning and sequencing of the amplicom. Following cell sorting into single clones, cells were screened by gDNA PCR, and monoallelic and biallelic cell lines were isolated. Furthermore, the induced deletion proved to interrupt the expression of the gene at the transcriptional level in a gene-dosage dependent manner where mono-allelic cell lines showed half level of expression compared to wild-type and bi-allelic cell lines showed levels close to zero. This effect lasted even after challenging with the virus or poly(I:C) the latter, a strong inductor of the innate response (FIGS. 8A, B and C).

To evaluate the impact of the deletion on vaccine production the H1N1 strain A/WSN/1933 was used at high and low multiplicity of infection (1 and 0.1 MOI respectively). Using this approach viral yield increases significantly in biallelic cell lines after ten hours of infection, around three times those levels found in the wild-type cell lines when measured in a plaque-forming units (PFU) assay. Virus isolated also showed five times higher TCID50s from biallelic cell lines when compared to the parental cell line (FIG. 8D).

Example 5

Screening and Identification of Antiviral Genes Against Hendra Virus

A number of genes relevant for virus production were identified in an siRNA screen investigating proteins required for Hendra virus (HeV) infection in human HeLa cells. HeLa cells (ATCC CCL-2) were maintained in growth medium (Eagles Modified Eagle Medium; EMEM) supplemented with 10% v/v foetal bovine serum (FBS), 10 mM HEPES, 2 mM L-glutamine and 100 U/ml penicillin, and 100 µg/mL streptomycin (P/S; Life Technologies). HeLa cells (7×10⁴) were reverse-transfected with siRNA pools (GE Life Sciences) using Dharmafect-1 (GE Life Sciences) in Opti-MEM (Life Technologies) overnight, after which media was removed and replaced with transfection media (growth media minus antibiotics) and cells incubated for a further 24 hours. Media was replaced ~6 hours post transfection (h.p.t.) and incubated for a further 18 hours. Cells were then infected with the Hendra Virus (HeV) (Hendra virus/Australia/Horse/1994/Hendra). For the 50% tissue culture infective dose (TCID50), 10-fold dilutions of tissue culture supernatants were made in medium in a 96-well tissue culture. Plates were incubated for 3 days (HeV) at 37° C. and 5% $CO_2$ and scored for cytopathic effect. The infectious titer was calculated by the method of Reed and Muench (1938). Viral replication for silenced genes was compared to a non-targeting siRNA control (siNT). A significant increase in viral replication was observed with silencing of a number of genes (see FIG. 9 and Table 2). Silencing of ADCY7 demonstrated the highest increase in viral titre (see Table 2).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

This application claims priority from Australian Provisional Application No. 2015904851 entitled "Production of viruses in cell culture" filed on 24 Nov. 2015, the entire contents of which are hereby incorporated by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

TABLE 2

Silencing of select genes increases Hendra Virus replication in HeLa cells

| | TCID50/mL (Hendra virus) | | |
|---|---|---|---|
| gene | AVERAGE | S.D | one-way ANOVA test |
| mock (negative control) | 953524 | 1024787 | N/A |
| siNEG (negative control) | 836250 | 701595 | N/A |
| PLK (positive control) | 747 | 801 | *** |
| ADCY7 | 53600 | 33069 | ** |
| AKAP10 | 3280 | 1022 | *** |
| ALX1 | 3896 | 4278 | *** |
| CBLN4 | 3730 | 1820 | *** |
| CRK | 110100 | 137444 | ** |
| CXorf56 | 86600 | 26800 | ** |
| DDX10 | 2236 | 1272 | *** |
| EIF2S3 | 1642 | 2015 | *** |
| ESF1 | 8510 | 8755 | ** |
| GBF1 | 10220 | 7996 | * |
| GCOM1 | 11190 | 7652 | * |
| GTPBP4 | 14460 | 8530 | * |
| HOXB9 | 127200 | 128378 | * |
| IFT43 | 43300 | 39147 | * |
| IMP4 | 1696 | 1206 | * |
| ISY1 | 1235 | 1317 | * |
| KIAA0586 | 1642 | 2015 | * |
| KPNA3 | 15250 | 13740 | * |
| LRRIQ1 | 36500 | 12139 | ** |

TABLE 2-continued

Silencing of select genes increases Hendra Virus replication in HeLa cells

| gene | TCID50/mL (Hendra virus) | | |
|---|---|---|---|
| | AVERAGE | S.D | one-way ANOVA test |
| LUC7L | 23700 | 10278 | ** |
| MECR | 814 | 900 | ** |
| MRPL12 | 43160 | 41593 | ** |
| POLR3E | 7970 | 9247 | ** |
| PWP2 | 23560 | 17198 | ** |
| RPL7A | 4620 | 3618 | ** |
| SERPINH1 | 16960 | 12057 | ** |
| SLC47A2 | 30300 | 11723 | ** |
| SMYD2 | 4740 | 3700 | ** |
| STAB1 | 11560 | 7150 | ** |
| TTK | 72300 | 96300 | ** |
| WNT3 | 30300 | 11700 | ** |
| XPO1 | 2740 | 1544 | ** |

REFERENCES

Bird et al. (1988) Science, 242:423-426.
Bannister et al. (2007) BMC Biotechnology. 7:79.
Constantini et al. (2008) Cancer Biotherm Radiopharm. 23: 3-24.
De Coupade et al. (2005) Biochem J, 390:407-418.
Deshayes et al. (2008) Adv Drug Deliv Rev. 60:537-547.
Grein et al. (2013) CHemie Ingenieur Technik 85(8):1183-1192.
Harmsen and De Haard (2007) Appl Microbiol Biotechnol. 77: 13-22.
Himly et al. (1998) Virology. 248(2):295-304/
Howl et al. (2007) Biochem Soc Trans. 35:767-769.
Huston et al. (1988) Proc Natl Acad Sci. USA. 85:5879-5883.
Jones (2008) Biotechnolo Prog. 24:807-814.
Josefsberg et al. (2012) Biotech and Bioengineering. 109(9) 1443-1460.
Kalbfuss et al. (2006) Biotech and Bioengineering. 97(1): 73-85.
Koppelhus et al. (2008) Bioconj Chem. 19:1526-1534.
Lodish et al. (2000) Molecular Cell Biology 4th Edition, New York, Section 12.5.
Lowenthal et al., (1995) J Interferon Cytokine Res. 15(11): 939-45.
Makarova et al. (2015) Nature Reviews Microbiology 13:1-15.
Massine et al. (2005) J Virol. 79(21):13811-13816.
Meyer-Losic et al. (2006) J Med Chem. 49:6908-6916.
Milian et al. (2015) BioMed Research International 1-11.
Morrison et al. (1984) Proc Natl Acad Sci USA 81:6851-6855.
Muyldermans (2001) J Biotechnol. 74:277-302.
Ran et al. (2013) Nature Protocols. 8:2281-2308
Reed and Muench (1938) The American Journal of Hygiene 27:493-497.
Smith et al. (2008) Vaccine. 26(29-30): 3778-3782.
Tibary et al. (2007) Soc Reprod Fertil Suppl. 64:297-313.
Weaver (2002) Molecular Biology 2nd Edition, New York, Section 22.1.
Wolf et al. (2008) Chem Eng Technol. 31(6):846-867.
Wolf et al. (2011) Expert Rev Vaccine. 10 (10): 1451-1475.
Zetsche et al. (2015) Cell 163:1-3.
Zhang et al. (2011) Nature Biotechnology 29:149-153.

The invention claimed is:

1. A method of replicating an Orthomyxoviridae virus, the method comprising:
   1) obtaining a population of cells having a genetic modification in the genome of the cells introduced by a programmable nuclease which knocks-out the expression of interferon alpha/beta receptor 1 (IFNAR1) in the cells when compared to isogenic cells lacking the genetic modification,
   2) inoculating the cells in vitro with the Orthomyxoviridae virus, and
   3) culturing the cells for a predetermined period of time to replicate the virus.

2. The method of claim 1, wherein the nuclease is selected from a: RNA-guided engineered nuclease (RGEN), transcription activator-like nuclease (TALEN) and zinc-finger nuclease (ZFN).

3. The method of claim 2, wherein the nuclease is a RNA-guided engineered nuclease (RGEN).

4. The method of claim 1, wherein the nuclease introduces a deletion, substitution or an insertion into the antiviral gene or a regulatory region thereof.

5. The method of claim 1, wherein the genetic modification is introduction of a transgene that encodes a polynucleotide that knocks-out the expression of IFNAR1 in the cell.

6. The method of claim 1, wherein the cells are selected from:
   1) from a primary cell line derived from chicken embryonic fibroblast (CEF);
   2) from a primary cell line derived from a chicken tissue,
   3) from an immortalized cell line from a chicken;
   4) from embryonic-derived stem cell line EB14;
   5) from embryonic-derived stem cell line EB66;
   6) from the immortalized chick embryo cell line PBS-1;
   7) from the chicken fibroblast cell line DF-1;
   8) Madin-Darby canine kidney (MDCK) cells;
   9) African green monkey kidney-derived Vero cells;
   10) human retina derived PER.C6 cells; and
   11) from the MRC-5 diploid cell line.

7. The method of claim 1, wherein the Orthomyxoviridae virus is selected from one or more of:
   i) an animal virus;
   ii) is selected from: an Influenza A virus, Influenza B virus, and Influenza C virus;
   iii) is the Influenza A virus; and
   iv) is selected from: H1N1, H1N2, H1N3, H1N4, H1N5, H1N6, H1N7, H1N9, H2N1, H2N2, H2N3, H2N4, H2N5, H2N7, H2N8, H2N9, H3N1, H3N2, H3N3, H3N4, H3N5, H3N6, H3N8, H4N1, H4N2, H4N3, H4N4, H4N5, H4N6, H4N8, H4N9, H5N1, H5N2, H5N3, H5N6, H5N7, H5N8, H5N9, H6N1, H6N2, H6N3, H6N4, H6N5, H6N6, H6N7, H6N8, H6N9, H7N1, H7N2, H7N3, H7N4, H7N5, H7N7, H7N8, H7N9, H9N1, H9N2, H9N3, H9N5, H9N6, H9N7, H9N8, H10N1, H10N3, H10N4, H10N6, H10N7, H10N8, H10N9, H11N2, H11N3, H11N6, H11N9, H12N1, H12N4, H12N5, H12N9, H13N2, H13N6, H13N8, H13N9, H14N5, H15N2, H15N8, H15N9 and H16N3.

8. The method of claim 7, wherein the animal is a human.

9. A method of producing a vaccine composition, the method comprising
   1) replicating a virus using the method of claim 1,
   2) harvesting the replicated virus or particles thereof from the cells, and
   3) preparing a vaccine composition from the harvested virus.

10. A population of cells in vitro comprising an Orthomyxoviridae virus and a genetic modification in the genome of the cells introduced by a programmable nuclease which knocks-out the expression of interferon alpha/beta receptor 1 (IFNAR1) gene in the cells.

11. A method of producing a population of cells of claim 10, the method comprising
1) introducing the genetic modification into one or more cells,
2) screening the cells produced from step 1) for the ability to produce more virus than an isogenic cell lacking the genetic modification,
3) selecting one or more cells with a genetic modification which produce more Orthomyxoviridae virus than an isogenic cell lacking the lacking the genetic modification, and
4) optionally clonally expanding the selected cells.

* * * * *